(12) United States Patent
Rodriguez et al.

(10) Patent No.: US 12,383,592 B1
(45) Date of Patent: *Aug. 12, 2025

(54) ENCAPSULATED CANNABINOID COMESTIBLE NOBLE METAL COMPOSITIONS AND PRODUCTS, METHODS OF PREPARING SAME

(71) Applicant: Kiffen, LLC, San Francisco, CA (US)

(72) Inventors: Sarah Rodriguez, San Francisco, CA (US); Ali Jamalian, San Francisco, CA (US)

(73) Assignee: Kiffen LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/421,784

(22) Filed: Feb. 8, 2024

Related U.S. Application Data

(63) Continuation of application No. 17/253,565, filed as application No. PCT/US2019/045517 on Aug. 7, 2019, now Pat. No. 12,036,258.

(60) Provisional application No. 62/716,233, filed on Aug. 8, 2018.

(51) Int. Cl.
| | |
|---|---|
| *A61K 36/185* | (2006.01) |
| *A61K 9/51* | (2006.01) |
| *A61K 47/46* | (2006.01) |

(52) U.S. Cl.
CPC .............. *A61K 36/185* (2013.01); *A61K 9/51* (2013.01); *A61K 47/46* (2013.01)

(58) Field of Classification Search
None
See application file for complete search history.

(56) References Cited

FOREIGN PATENT DOCUMENTS

WO    WO 2017/130046    *    8/2017

* cited by examiner

*Primary Examiner* — Michael V Meller
(74) *Attorney, Agent, or Firm* — Staniford Tomita LLP

(57) ABSTRACT

A method for the micro-encapsulation of terpenes, lipids, sterols, antioxidants, cannabinoids and/or other hydrophobic compounds includes providing an extract material and preparing an aqueous solution including a cellular material. A disruption of the aqueous solution is performed, to at least partially liberate proteins of the cellular material. The extract material and the disrupted aqueous solution are combined to form an intermediate mixture. The intermediate mixture is disrupted to form an encapsulated mixture, and a pH of the encapsulated mixture is reduced. The encapsulated mixture is then dried and combined with a comestible noble metal, to form a finished product.

20 Claims, 23 Drawing Sheets

ENCAPSULATED CANNABINOID COMESTIBLE NOBLE METAL COMPOSITIONS AND PRODUCTS, METHODS OF PREPARING SAME

CROSS-REFERENCE TO RELATED APPLICATIONS

This application is a continuation patent application of U.S. patent application Ser. No. 17/253,565, "Encapsulated Cannabinoid Comestible Noble Metal Compositions And Products, Methods Of Preparing Same" filed Dec. 17, 2020, now US Patent No. 3 which is a 371 of PCT/US2019/045517, "Encapsulated Cannabinoid Comestible Noble Metal Compositions And Products, Methods Of Preparing Same" filed Aug. 7, 2019 which claims priority to U.S. Provisional Patent Application No. 62/716,233, "Encapsulated Cannabinoid Comestible Noble Metal Compositions And Products, Methods Of Preparing Same" filed Aug. 8, 2018 all of which are hereby incorporated by reference in their entireties.

FIELD

The present disclosure relates to noble metal/cannabinoid products and formulations, and methods of preparing said noble metal/cannabinoid products and formulations.

BACKGROUND

*Cannabis* is a genus of flowering plants that includes at least three species, *Cannabis sativa, Cannabis indica,* and *Cannabis ruderalis. Cannabis* plants include secondary metabolites called cannabinoids. Cannabinoids are hydrophobic, and can act on cannabinoid receptors in tissues and cells of the human body.

SUMMARY

In some embodiments of the present disclosure, methods for the production of encapsulated cannabinoids (and/or other hydrophobic compounds) comestible noble metal compositions and products suitable for medicinal, pharmaceutical, nutraceutical, edible, cosmetic, topical, and food applications. The production of such compositions and products can include the preparation of a plant-based and microbial-based suspension, and a microencapsulation of the active (e.g., plant) material with the microbial material, which can then be formed and/or combined with a comestible noble metal, such as metallic gold and/or metallic silver. In other embodiments, production of a compositions and products includes processing an active material (e.g., crumble or shatter material), which can include, depending on the implementation, decarboxylating the active material. A microbial material, such as *Spirulina*, can then be added to the active material (e.g., directly to decarboxylated shatter) with an aqueous solution (e.g., water, having a temperature above 25° C., such as a temperature of between about 32° C. to about 45° C.) and mixing (e.g., at 500 rpm, 1000 rpm, 1500 rpm, 2000 rpm, 2500 rpm, or 3000 rpm, by way of non-limiting example) to produce a first mixture. The first mixture can then be further processed, such as via sonication and/or multiple sonication steps (e.g., sonication for about 20 minutes at about 4° C., then sonication for about 60 minutes at about 60° C.). In some embodiments, an emulsifier (such as lecithin) and/or humectant (such as a polyol, e.g., glycerol) can be added to the processed (e.g., sonicated) first mixture to provide a second mixture, which can be further processed (e.g., sonicated). The processed second mixture can then be formed into a sheet or other form, e.g., poured over a surface to form a free-form layer, extruded as a sheet, etc., which can then be dehydrated to form a dehydrated sheet, to which a comestible noble metal sheet or leaf can be applied to at least one surface thereof (in some embodiments, at least two surfaces), resulting in a finished or substantially finished product. The use of a comestible noble metal can, in some embodiments, reduce or prevent bioburden on the finished product by preventing or slowing the growth of microbes/bacteria, e.g., via oligodynamic mechanisms.

In some embodiments, a method includes providing a *Cannabis* extract material including a shatter, a crumble, a budder, an oil (e.g., butane hash oil, propane hash oil), nug run concentrate, CO2 concentrate, rosin, trim run, live resin, sap, dry sift, ice water hash, full melt, wax, pull and snap, fraction, THC, CBD, or any other product resulting from an extraction of hydraulic press operation applied to plant, or a synthetic material that includes a *Cannabis* derivative. The method also includes providing distilled water, and raising a pH of the distilled water to a value of about 9 to about 10, to produce a raised-pH water. An aqueous solution, including the raised-pH water and *Spirulina* (Arthrospira *platensis,* and/or Arthrospira maxima) or components thereof, is prepared, the aqueous solution having about 3% weight *Spirulina* per volume. The aqueous solution is blended. The blended aqueous solution is ultrasonicated to at least partially liberate proteins of the *Spirulina*, thereby producing a membrane-disrupted *Spirulina* solution (i.e., where at least a portion of the *Spirulina* cell membrane has been disrupted, e.g., resulting in liberation of cellular component/contents of the *Spirulina*). The *Cannabis* extract material and the disrupted *Spirulina* solution are combined, in a ratio of about 1:1, to form an intermediate mixture. The intermediate mixture is ultrasonicated to form a first mixture including the *Cannabis* extract material encapsulated by the *Spirulina* or a derivative thereof. Citric acid is added to the first mixture to produce a reduced-pH mixture having a pH of about 3. The reduced-pH mixture is dispensed (e.g., poured) onto a substrate to form a layer including about 2.5 mL of the reduced-pH mixture per square inch. The layer is dehydrated form and combined with a comestible noble metal a finished product.

A method for the micro-encapsulation of terpenes, lipids, sterols, antioxidants, cannabinoids and/or other hydrophobic compounds includes providing an extract material (e.g., a shatter, a crumble, or a butter) and preparing an aqueous solution including a cellular material (e.g., *Spirulina*). Preparing the aqueous solution can include increasing a pH of distilled water to produce a raised-pH water, and combining the raised-pH water with the cellular material. A disruption of the aqueous solution is performed (e.g., via ultrasonication), to at least partially liberate proteins of the cellular material. The extract material and the disrupted aqueous solution are combined to form an intermediate mixture. The intermediate mixture is disrupted to form an encapsulated mixture, for example via cold ultrasonication (i.e., at or below room temperature, e.g., for a duration of about 2 hours, or about 3 hours, or about 4 hours, or about 5 hours, or from about 3 hours to about 4 hours, or from about 3.5 hours to about 4.5 hours), or via heated ultrasonication (e.g., at a temperature of about 40° C., about 50° C., about 60° C., about 62° C., about 64° C., about 66° C., about 68° C., about 69° C., about 71° C., about 70° C., about 73° C., about 75° C., about 79° C., about 81° C., about 83° C., or about 85° C., or between about 60° C. and about 75° C., or between about 60° C. and about 75° C.) (e.g., for a duration of not more than about 10 minutes, not more than about 15 minutes, not more than about 20 minutes, not more than about 30 minutes, not more than about 43 minutes, not more than about 45 minutes, not more than about 47 minutes, between about 40 minutes and about 50 minutes, not more than about 1 hour, not more than about 2 hours, not more than about 2.5 hours, or not more than about 3 hours, or not more than about 4 hours, or about 4 hours, or from about 3 hours to about 4 hours, or from about 3.5 hours to about 4.5 hours, or not more than about 5 hours). A pH of the encapsulated mixture is reduced. The encapsulated mixture is then dried, to form a finished product.

In some embodiments, the method also includes decarboxylating the extract material before combining the extract material and the disrupted aqueous solution.

In some embodiments, drying the encapsulated mixture includes pouring the encapsulated mixture onto a substrate (e.g., silicone), and dehydrating the poured encapsulated mixture. The dehydrating can be performed at a temperature of about 165° F. and for a duration of at least about 15 hours.

In some embodiments, drying the encapsulated mixture includes lyophilization of the encapsulated mixture.

In some embodiments, drying the encapsulated mixture is performed under vacuum.

In some embodiments, drying the encapsulated mixture is performed at a temperature of from about 10° C. to about 100° C.

In some embodiments, drying the encapsulated mixture includes nano-spray drying.

In some embodiments, the method also includes blending the aqueous solution before performing the disruption of the aqueous solution.

In some embodiments, a method for the nano-encapsulation and/or micro-encapsulation of terpenes, lipids, sterols, antioxidants, cannabinoids and/or other hydrophobic compounds includes receiving distilled water and one or more *Cannabis* extract materials, such as a shatter, a wax, a crumble, or a butter. A pH of the distilled water is raised to a value of about 9 to about 10, to produce a raised-pH water. An aqueous solution, including the raised-pH water and *Spirulina*, is prepared such that the aqueous solution has about 3% weight *Spirulina* per volume. In some such implementations, the *Cannabis* extract material includes the wax, and the wax has about 3% THC. Preparing the aqueous solution can also include at least one of mixing and ultrasonicating. Depending upon the intended application, the method can also include diluting the aqueous solution to a predetermined/desired dilution level (e.g., about 1:1,000, about 1:10,000, about 1:20,000, about 1:100,000, about 1:200,000, etc.).

In some embodiments, a method for the nano-encapsulation and/or micro-encapsulation of terpenes, lipids, sterols, antioxidants, cannabinoids and/or other hydrophobic compounds includes receiving distilled water and a *Cannabis* extract material including a shatter, a crumble, or a butter. A pH of the distilled water is raised to a value of about 9 to about 10, to produce a raised-pH water. An aqueous solution, including the raised-pH water and *Spirulina*, is prepared such that the aqueous solution has about 3% weight *Spirulina* per volume. The aqueous solution is blended, and ultrasonicated to at least partially liberate proteins of the *Spirulina*, thereby producing a disrupted *Spirulina* solution. The *Cannabis* extract material and the disrupted *Spirulina* solution are combined, in a ratio of about 1:1, to form an intermediate mixture. The intermediate mixture is sonicated to form a first mixture including encapsulated *Cannabis* extract material. In some embodiments, the mixture is dispensed onto a substrate to form a layer including about 2.5 mL of the reduced-pH mixture per square inch. The layer is then dehydrated to form an encapsulated material. In other embodiments, another additive such as soy lecithin (e.g., ~1%) may be added to the first mixture before dispensing onto the substrate and forming the layer (e.g., to impact "mouthfeel" of a finished product). In still other embodiments, citric acid may be added to the first mixture to produce a reduced-pH mixture having a pH of about 3 before dispensing onto the substrate and forming the layer. The encapsulated material can subsequently be combined with a solvent to form a liquid finished product, which, for example, can be a solution or a suspension.

In some implementations, a centrifuging step is performed after ultrasonication, to remove broken cell membrane from the disrupted *Spirulina* solution, leaving only or substantially only protein behind for the subsequent solubilization/encapsulation of the wax (e.g., to modify a texture of the finished product).

In some embodiments, a method for the nano-encapsulation and/or micro-encapsulation of terpenes, lipids, sterols, antioxidants, cannabinoids and/or other hydrophobic compounds includes providing an extract material, and preparing an aqueous solution including a cellular material. A disruption of the aqueous solution is performed, to at least partially liberate proteins of the cellular material. The extract material and the disrupted aqueous solution are combined to form an intermediate mixture, and a disruption of the intermediate mixture is performed, so as to form an encapsulated mixture. In some embodiments, the encapsulated mixture is a liquid finished product (e.g., a solution or a suspension). In other embodiments, a pH of the encapsulated mixture is reduced to form a liquid finished product, which, for example, can be a solution or a suspension.

In some embodiments, a method for preparing a noble metal-bearing finished product includes providing a shatter material, and decarboxylating the shatter material (e.g., at about 115° C. for 40 minutes). *Spirulina* is added directly to the decarboxylated shatter, and water, having a temperature of about 32° C. to about 45° C., is added to the combined *Spirulina* and decarboxylated shatter. The combined warm water, *Spirulina* and decarboxylated shatter are mixed (e.g., at about 2,000 rpm), to produce a first mixture. The first mixture is sonicated twice: (1) at a first temperature for a first duration (e.g., about 20 minutes at about 4° C.), and (2) at a second temperature for a second duration (e.g., about 60 minutes at about 60° C.). A predetermined amount of at least one of lecithin or glycerol is then added to the sonicated first mixture, to produce a second mixture, and the second mixture is sonicated. The sonicated second mixture is poured over a surface to form a free-form layer, and the free-form layer is dehydrated to produce a dehydrated layer. At least one of gold or silver is applied to at least one surface of the dehydrated layer (e.g., via adhesion of comestible metal leaf, spray-application of a comestible metal film, etc.), to form a finished product.

DETAILED DESCRIPTION

Figure 1A:
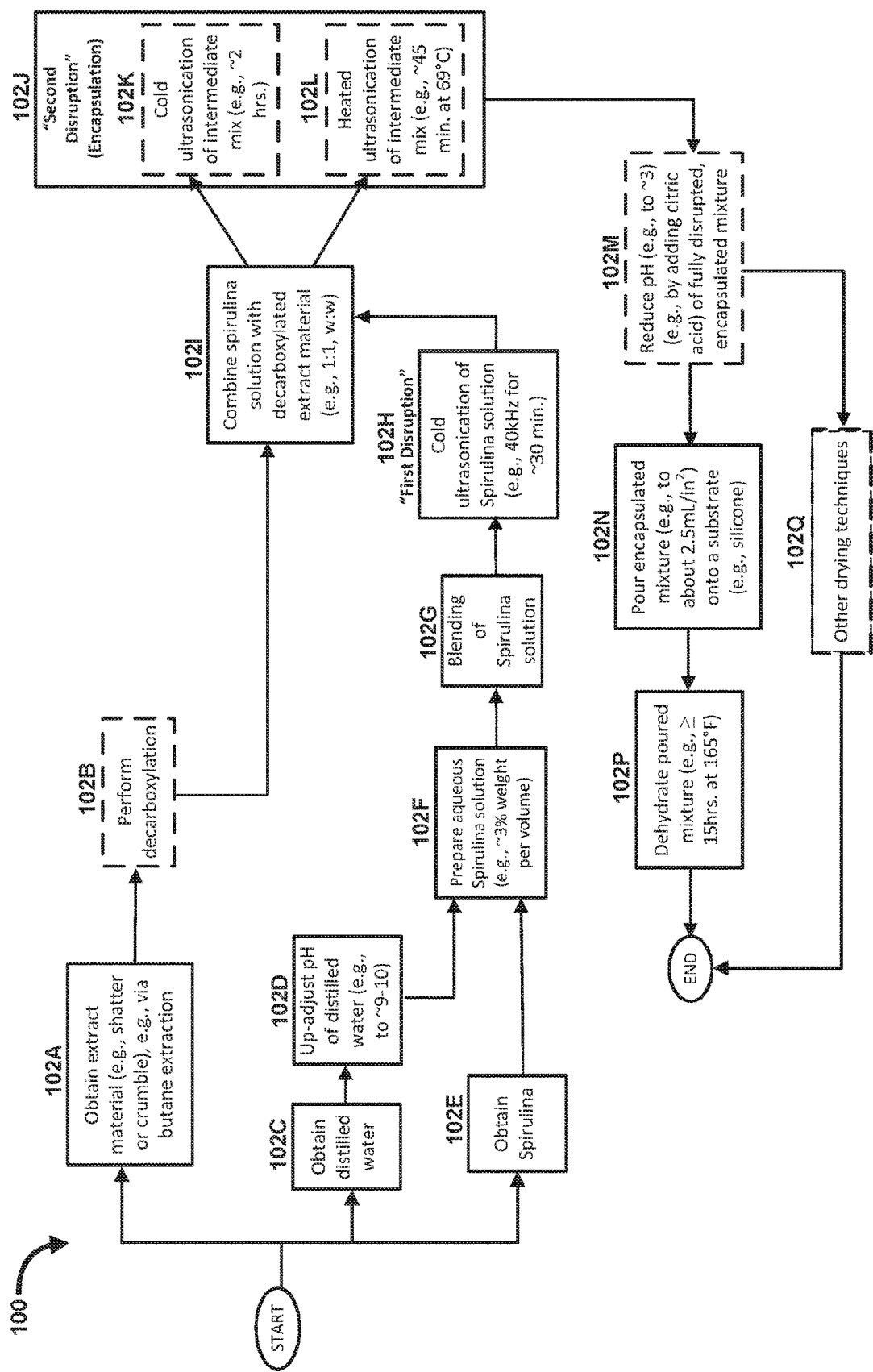
FIG. 1A is a process flow diagram illustrating a method for encapsulation of an extract material, according to some embodiments.

The present disclosure is directed to methods and systems for the micro-encapsulation of hydrophobic compounds and/or lipophilic compounds, and/or materials, such as extracts or synthetics, that include one or more hydrophobic and/or lipophilic compounds as well as one or more neutral and/or hydrophilic compounds, including but not limited to terpenes, terpenoids, lipids, sterols, antioxidants, cannabinoids, and/or the like, and/or various combinations of various neutral, hydrophilic, and lipophilic/hydrophobic compounds. Embodiments includes methods for micro-encapsulation and/or otherwise stabilizing such compounds using microbial (including algae, for example a cyanobacteria, eukaryote, prokaryote, etc.), bacteria, protozoa, fungi (unicellular or multicellular), plant cells, cellular material, and/or components derived therefrom, and/or one or more naturally or synthetically derived compounds related to one or more microbe and/or plant cellular compounds (e.g., proteins), as well as to the resulting outputs of such methods, and products including/incorporating outputs of the method (s) in finished end products thereof. Applications of the methods, compounds, microencapsulated compounds, and finished end products as set forth herein include, by way of non-limiting example, health and medicinal, pharmaceutical, supplements, nutraceuticals, cosmetics, edible materials, and food applications.

According to the National Cancer Institute, the cannabinoid delta-9-THC in *Cannabis*, may relieve pain, lower inflammation and decrease anxiety. *Cannabis* and cannabinoids have been implicated in the relief of anxiety, nausea, pain, and the improvement of appetite. Due to these properties, *Cannabis* and cannabinoids may have use in treating symptoms of cancer and the side effects of cancer therapies. The U.S. Food and Drug Administration (FDA) has approved two cannabinoids, dronabinol and nabilone, for the treatment and prevention of nausea and vomiting, which are possible side effects of chemotherapy. Furthermore, laboratory studies have shown the capacity of *Cannabis* to selectively kill cancer cells. For example, one study suggests that some cannabinoids can provide a well-tolerated, promising therapeutic for the treatment of seizures in those with epilepsy. Additionally, cannabinoids have been implicated for the treatments of Alzheimer's Disease, ALS, Chronic Pain, Diabetes Mellitus Dystonia, Epilepsy, Fibromyalgia, GI Disorders, Gliomas/Cancer, Hepatitis C, HIV, Huntington's Disease, Hypertension, Incontinence, MRSA, Multiple Sclerosis, Osteoporosis, Pruritus, Rheumatoid Arthritis, Sleep Apnea and Tourette's Syndrome.

Water-based solutions, having compounds dissolved therein, are easier to deliver orally and via injection, when compared to non-aqueous solutions. However, the incorporation of compounds that are hydrophobic and/or lipophilic into water-based solutions has historically been difficult, as discussed below.

Difficulty of Formulation and Delivery of Cannabinoids and Other Hydrophobic Compounds The physical properties of lipophilic/hydrophobic compounds, such as most cannabinoids, as well as many other hydrophobic medicinal and nutraceutical compounds, present distinct challenges for handling, formulation, and dosing. For example, incorporation of a lipophilic/hydrophobic compound (or compounds) in aqueous solution formulations can be difficult, as well as time and resource intensive. Moreover, such solutions can be difficult to reproduce consistently, distribute evenly/uniformly, etc. In some instances, it can even lead to poor adsorption within an aqueous environment, and this poor solubility in aqueous or polar solutions can, in turn, lead to low or inconsistent dosing and/or bioavailability (e.g., oral bioavailability). Moreover, such lipophilic/hydrophobic compounds can be difficult to dispense and accurately measure, often sticking to containers (e.g., glass or plastic containers), including when in aqueous solution, and thus further increasing the difficulty in delivering and/or integrating such compounds as part of a formulation.

Traditional methods of solubilizing hydrophobic compounds include the use of added edible detergent-like compounds and surfactants.

Cellular Material Encapsulation of Extract Materials

Embodiments of the present disclosure address the problems outlined above, and facilitate the solubilization, suspension, and/or micro-encapsulation of lipid, terpene, sterol, cannabinoid, and/or other generally non-polar, lipophilic and/or hydrophobic compounds, as well as mixtures/compounds containing such compounds as well as one or more neutral and/or hydrophilic compounds therein, in some embodiments, without the use of added or synthetic detergents and/or surfactants, to produce finished products, including in some instances, finished products that are suitable for consumption. Some encapsulation/micro-encapsulation/stabilization (generally "micro-encapsulation" or "micro-encapsulated") methods set forth herein utilize whole cells and extractions of whole cells ("cellular material"), rather than a single substance or molecule, thereby utilizing a mixture of one or more of lipids, proteins, and/or nucleic acid for encapsulation of hydrophobic material. A finished product (also referred to as a "final substance," a "consumable," a "composition," or a "concentrate") produced by methods set forth herein can include an extract, oil, or wax (e.g., one or more lipid, fatty, sterol, non-polar, lipophilic, and/or hydrophobic compounds) that is micro-encapsulated by cellular material and/or components of cellular material, in some embodiments, that is micro-encapsulated by cellular material and/or components of cellular material in one or more polar solvents. Moreover, in some embodiments, finished products produced and/or facilitated by methods set forth herein exhibit high uniformity (e.g., in texture, in low occurrence of lipid droplets, etc.), and/or can be configured to be partially, substantially, or fully water-soluble, and/or can be used as a "concentrate"

(including one or more components of extract material), e.g., for incorporation into one or more edible, topical, or otherwise consumable products.

In some embodiments, lipophilic/hydrophobic compounds of the disclosure can include terpenes, sterols, cannabinoids, and other compounds of medicinal and nutraceutical value/application. Examples of terpenes include but are not limited to nerolidol, limonene, pinene, alpha-pinene, d-linalool, myrcene, ocimene, terpinolene, terpineol, valencene, caryophyllene, BCP, alpha humulene, phellandrene, carene, fenchol, terpinene, borneol, bisabolol, phytol, camphene, sabinene, camphor, isoborneol, cedrene, guaiol, pulegone, isopulegol, cymene, terpineol, and/or the like. Examples of classes of plant sterols types include but are not limited to sterol esters, stanols and pro-sterols. Examples of lipids include but are not limited α-linolenic acid, arachidonic acid, eicosapentaenoic acid, and docosahexaenoic acid. Examples of antioxidants include zeaxanthin, lutein, α-carotene, fucoxanthin astaxanthin, canthaxanthin, and b-carotene.

Cannabinoids according to the disclosure can include, while not being limited to those obtained or obtainable from *Cannabis* plants, which can include, by way of non-limiting example: Δ9-Tetrahydrocannabinol (Δ9-THC), Δ8-Tetrahydrocannabinol (Δ8-THC), Cannabichromene (CBC), Cannabicyclol (CBL), Cannabidiol (CBD), Cannabielsoin (CBE), Cannabigerol (CBG), Cannabinidiol (CBND), Cannabinol (CBN), Cannabitriol (CBT), and their propyl homologs, including, by way of non-limiting example cannabidivarin (CBDV), Δ9-Tetrahydrocannabivarin (THCV), cannabichromevarin (CBCV), and cannabigerovarin (CBGV). Cannabinoids according to the disclosure can also include those produced by plants (also known as phytocannabinoids, natural cannabinoids, herbal cannabinoids, or classical cannabinoids). Cannabinoids of the disclosure can include synthetic cannabinoids, and/or cannabinoids isolated from *Cannabis* plants, by way of non-limiting example, Tetrahydrocannabinol (THC), Cannabidiol (CBD) (e.g., derived from *Cannabis indica*, *Cannabis ruderalis*, or *Cannabis sativa* ("hemp")), CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), and CBGM (Cannabigerol Monomethyl Ether). In the *Cannabis* plant, cannabinoids are synthesized and accumulated as cannabinoid acids (e.g., cannabidiolic acid (CBDA)), and drying and/or heating can cause such acids to decarboxylize (e.g., CBDA to CBD).

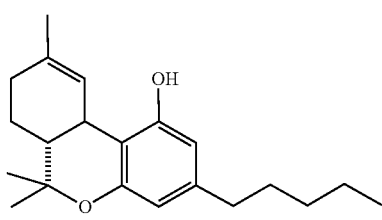

Tetrahydrocannabinol (THC)

Known as delta-9-tetrahydrocannabinol (Δ9-THC), THC is the principal psychoactive constituent (or cannabinoid) of the *Cannabis* plant. The initially synthesized and accumulated form in plant is THC acid (THCA). THC has mild to moderate analgesic effects, and *Cannabis* can be used to treat pain by altering transmitter release. Other effects include relaxation, alteration of visual, auditory, gustatory, and olfactory senses, fatigue, and appetite stimulation, as well as anti-nausea effects.

In the *Cannabis* plant, THC occurs mainly as tetrahydrocannabinolic acid (THCA, 2-COOH-THC). Geranyl pyrophosphate and olivetolic acid react, catalyzed by an enzyme to produce cannabigerolic acid, which is cyclized by the enzyme THC acid synthase to give THCA. Over time, or when heated, THCA is decarboxylated producing THC. The pathway for THCA biosynthesis is similar to that which produces the bitter acid humulone in hops.

Non-Limiting Examples of THC Variants Include:

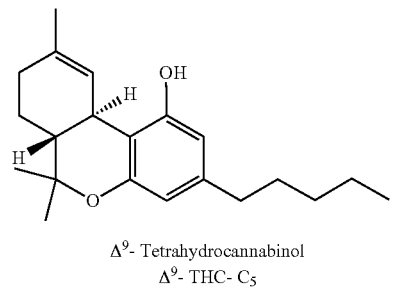

Δ9- Tetrahydrocannabinol
Δ9- THC- $C_5$

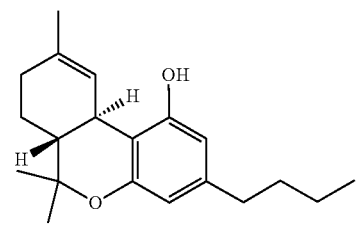

Δ9- Tetrahydrocannabinol-$C_4$
Δ9- THC- $C_4$

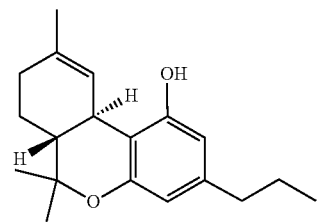

Δ9- Tetrahydrocannabivarin
Δ9- THCV- $C_3$

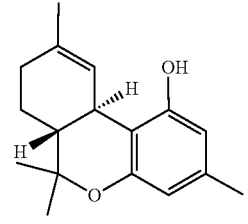

Δ9- Tetrahydrocannabiorcol
Δ9- THCI- $C_1$

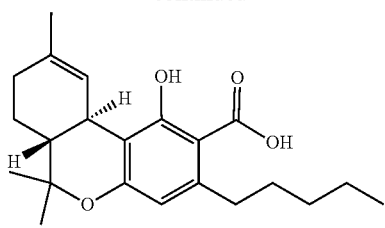

Δ⁹- Tetrahydro-cannabinolic acid A
Δ⁹- THCA- $C_5$A

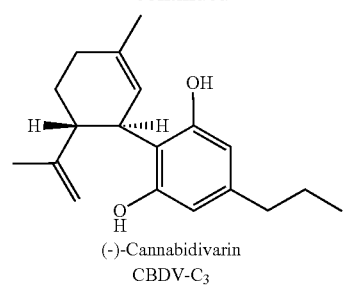

(-)-Cannabidivarin
CBDV-$C_3$

CBD is another cannabinoid found in *Cannabis*, and has been shown to act as an indirect antagonist of cannabinoid agonists, and has also been shown to act as a 5-HT1A receptor agonist, an action which is potentially involved in antidepressant, anxiolytic, and neuroprotective effects. CBD is also an allosteric modulator at the Mu and Delta opioid receptor sites. *Cannabis* produces CBD-carboxylic acid through the same metabolic pathway as THC, until the last step, where CBDA synthase performs catalysis instead of THCA synthase. Non-limiting examples of CBD variants include:

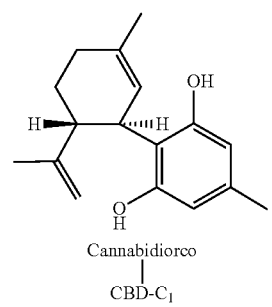

Cannabidiorco
CBD-$C_1$

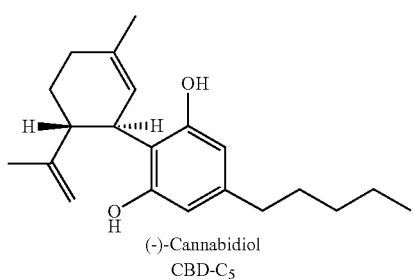

(-)-Cannabidiol
CBD-$C_5$

CBG is another cannabinoid found in *Cannabis*, and is generally considered to be low or non-psychoactive. CBG can be found in higher concentrations in hemp rather than in varieties of *Cannabis* cultivated for high THC content and their corresponding psychoactive properties. CBG has been found to act as a high affinity a2-adrenergic receptor agonist, moderate affinity 5-HT1A receptor antagonist, and low affinity CB1 receptor antagonist. CBG also binds to the CB2 receptor. CBG has been shown to relieve intraocular pressure, useful in the treatment of glaucoma. Non-limiting examples of CBG variants include:

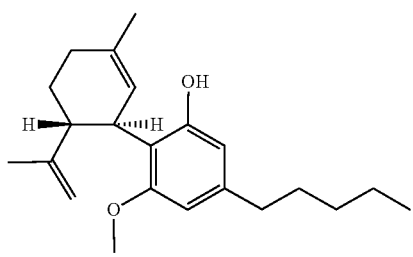

Cannabidol
momomethyl ether
CBDM-$C_5$

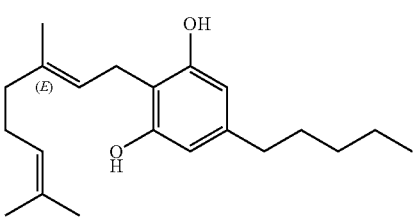

Cannabigerol
(E)-CBG-$C_5$

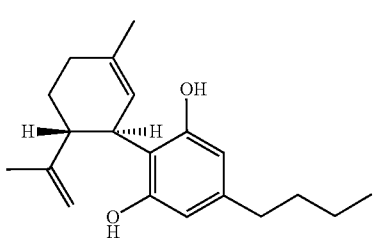

Cannabidiol-$C_4$
CBD-$C_4$

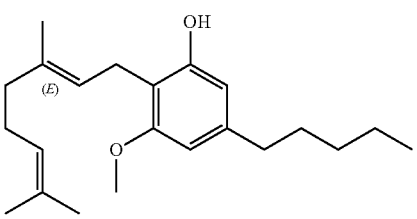

Cannabigerol
monomethyl ether
(E)-CBGM-$C_5$A

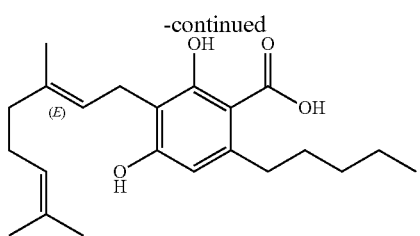

Cannabinerolic acid A
(Z)-CBGA-C₅ A

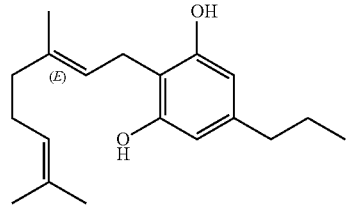

Cannabigerovarin
(E)-CBGV-C₃

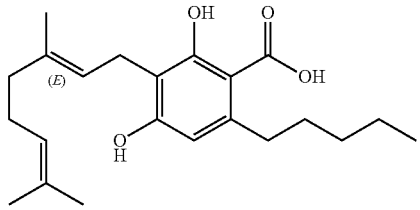

Cannabinerolic acid A
(E)-CBGA-C₅ A

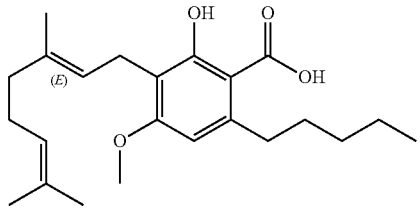

Cannabigerolic acid A
monomethyl ether
(E)-CBGAM-C₅ A

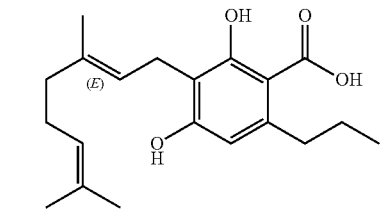

Cannabigerovarinic acid A
(E)-CBGVA-C₃ A

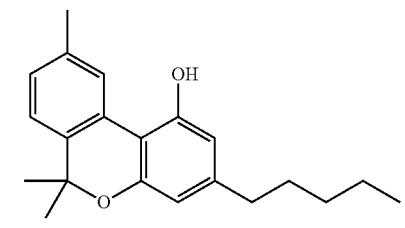

Cannabinol (CBN)

CBN is a psychoactive cannabinoid found in *Cannabis*, particularly *Cannabis sativa* and *Cannabis* indica/*afghanica*. It is also a metabolite derived from tetrahydrocannabinol (THC). CBN acts as a weak agonist of the CB1 and CB2 receptors, with lower affinity in comparison to THC. Non-limiting examples of CBN variants include

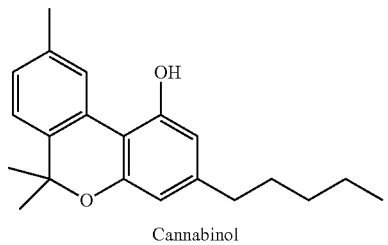

Cannabinol
CBN-C₅

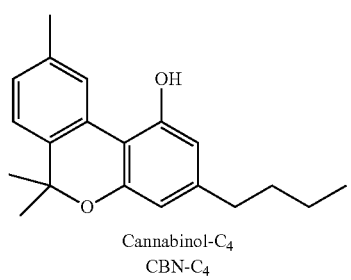

Cannabinol-C₄
CBN-C₄

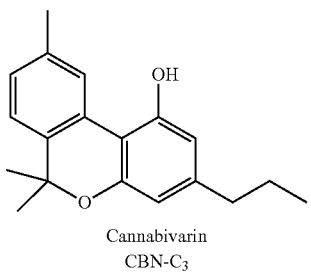

Cannabivarin
CBN-C₃

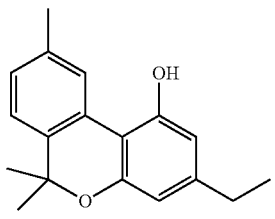

Cannabinol-C₂
CBN-C₂

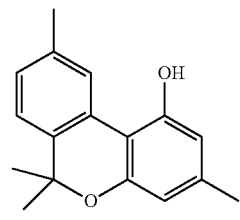

Cannabiorcol
CBN-C₁

-continued

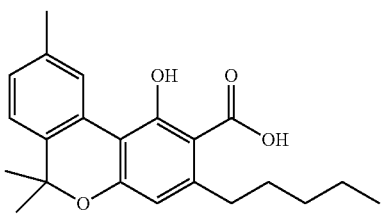

Cannabinolic acid A
CBNA-C5A

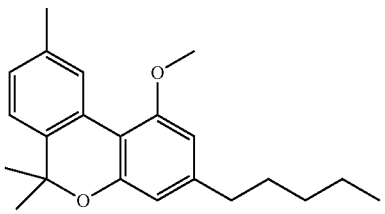

Cannabinol methyl ether
CBNM-C5

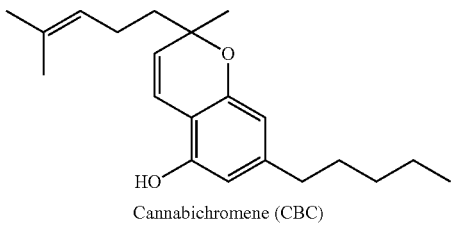

Cannabichromene (CBC)

CBC has structural similarity to the other natural cannabinoids, including tetrahydrocannabinol, tetrahydrocannabivarin, cannabidiol, and cannabinol, among others. CBC may play a role in the anti-inflammatory and anti-viral effects of *Cannabis*, and may contribute to the overall analgesic effects of *Cannabis*. Non-limiting examples of CBC variants include:

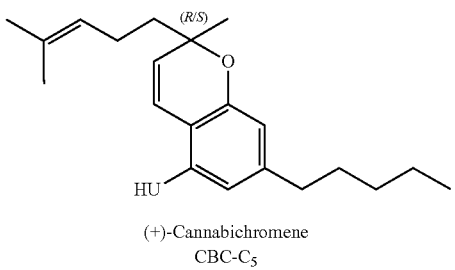

(+)-Cannabichromene
CBC-C5

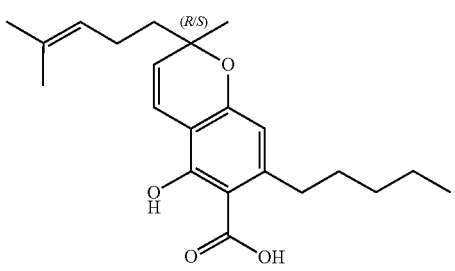

(+)-Cannabichromenic
acid A
CBCA-C5A

-continued

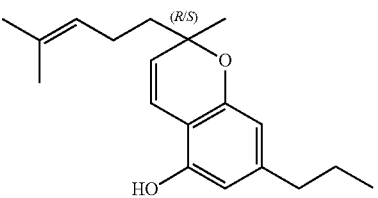

(±)-Cannabivarichromene,
(+)-Cannabichromevarin,
CBCV-C3

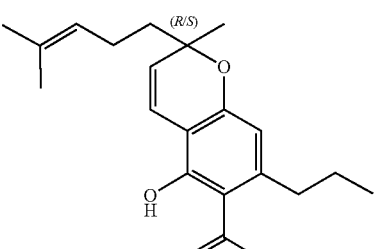

(+)-Cannabichromevarinic
acid A
CBCVA-C3A

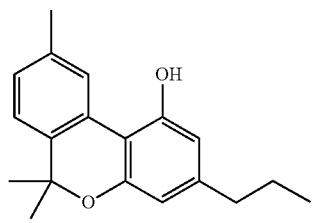

Cannabivarin (CBV)

CBV is a cannabinoid found in minor amounts in *Cannabis*, and is generally considered to have low or no psychoactivity. It is an analog of cannabinol (CBN) with the side chain shortened by two methylene bridges (-CH2-). CBV is an oxidation product of tetrahydrocannabivarin (THCV, THV).

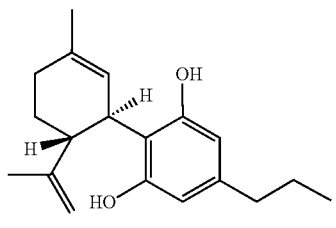

Cannabidivarin (CBDV)

CBDV is a cannabinoid found in *Cannabis*, and is generally considered to have low or no psychoactivity. It is a homolog of cannabidiol (CBD), with the side-chain shortened by two methylene bridges (CH2 units).

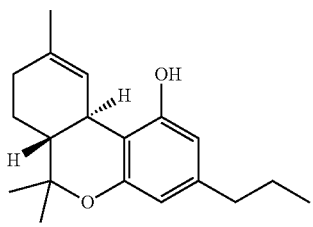

Tetrahydrocannabivarin (THCV, THV)

THCV, or THV is a homologue of tetrahydrocannabinol (THC) having a propyl (3-carbon) side chain. This terpenophenolic compound can be found naturally in *Cannabis*, sometimes in significant amounts. Plants with elevated levels of propyl cannabinoids (including THCV) have been found. THCV has been shown to be a CB1 receptor antagonist.

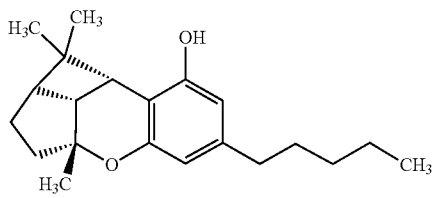

Cannabicyclol (CBL)

Cannabicyclol (CBL) is a cannabinoid found in the *Cannabis* species. CBL is a degradative product like cannabinol. Light converts cannabichromene to CBL. Non-limiting examples of CBL variants include:

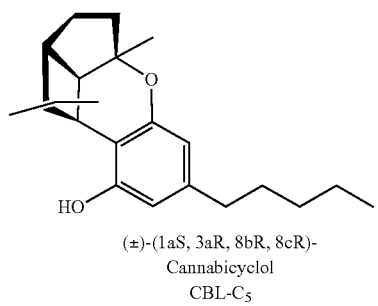

(±)-(1aS, 3aR, 8bR, 8cR)-
Cannabicyclol
CBL-$C_5$

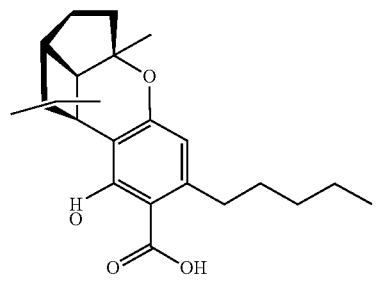

(±)-(1aS, 3aR, 8bR, 8cR)-
Cannabicyclolic acid A
CBLA-$C_5$A

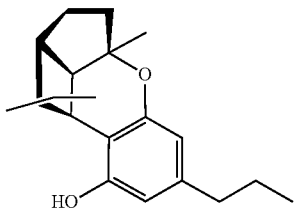

(±)-(1aS, 3aR, 8bR, 8cR)-
Cannabicyclovarin
CBLV-$C_3$

Non-Limiting Examples of CBT Variants Include:

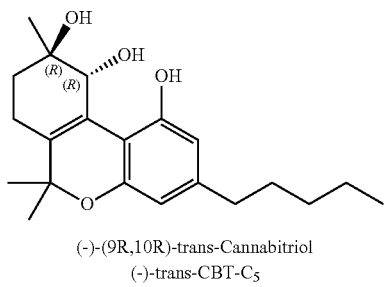

(-)-(9R,10R)-trans-Cannabitriol
(-)-trans-CBT-$C_5$

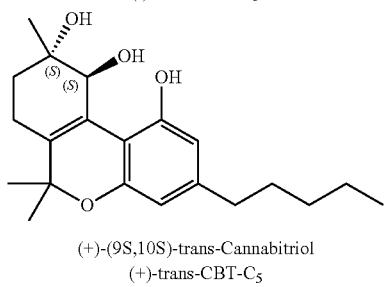

(+)-(9S,10S)-trans-Cannabitriol
(+)-trans-CBT-$C_5$

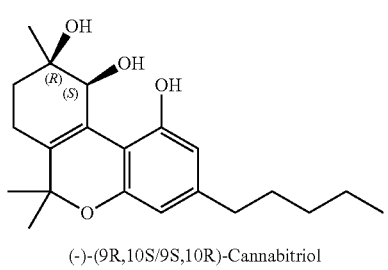

(-)-(9R,10S/9S,10R)-Cannabitriol
(±)-cis-CBT-$C_5$

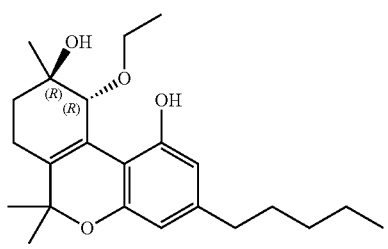

(-)-(9R,10R)-trans-10-O-Ethyl-
cannabitriol (-)-trans-CBT-OEt-$C_5$

-continued

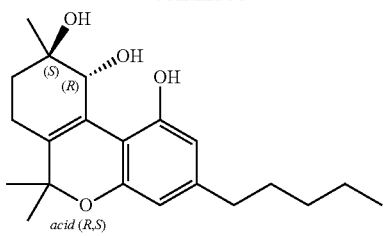

(=)-(9R,10R/9S,10S)-Cannabitriol-C₃
(±)-trans-CBT-C₃

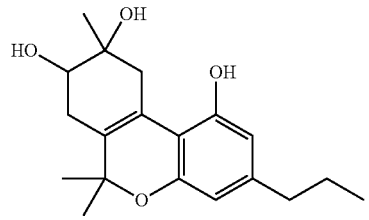

8,9-Dihydroxy-Δ⁶ᵃ⁽¹⁰ᵃ⁾-
tetrahydrocannabinol
8,9-Di-OH-CBT-C₅

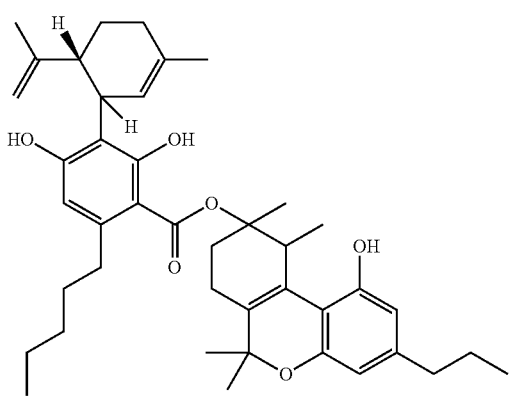

Cannabidiolic acid A
cannabitriol ester
CBDA-C₅ 9-OH-CBT-C₅ ester

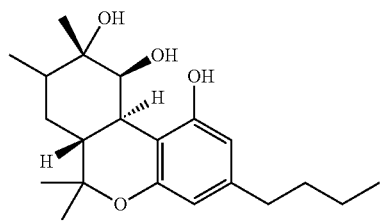

(-)-(6aR,9S,10S,10aR)-9,10-Dihydroxy-
hexahydrocannabinol, Cannabiripsol
Cannabiripsol-C₅

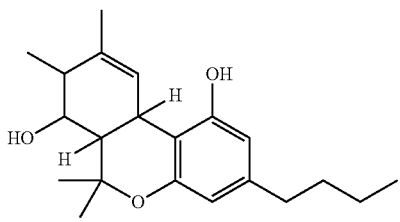

(-)-(6a,7,10a-Trihydroxy-Δ⁹-
tetrahydrocannabinol (-)-Cannabitetrol

-continued

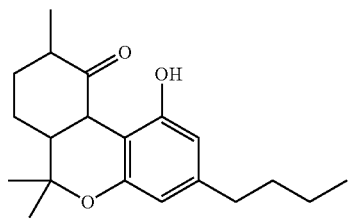

10-Oxo-Δ⁶ᵃ⁽¹⁰ᵃ⁾-
tetrahydrocannabinol OTHC

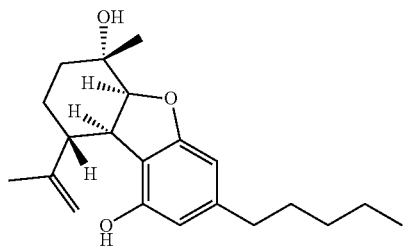

Cannabielsoin-type (CBE)

Non-Limiting Examples of CBE Variants Include:

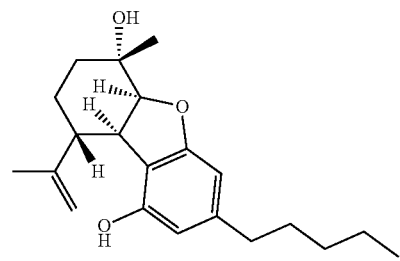

(5aS, 6S, 9R, 9aR)-Cannabielsoin
CBE-C₅

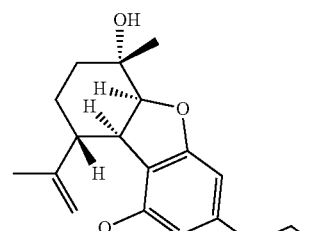

(5aS, 6S, 9R, 9aR)-C₃-Cannabielsoin
CBE-C₃

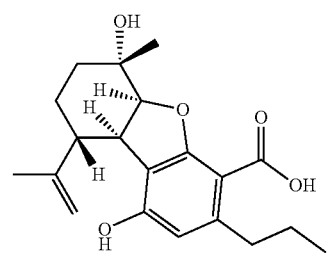

(5aS, 6S, 9R, 9aR)-Cannabielsoic acid A
CBEA-C₅A

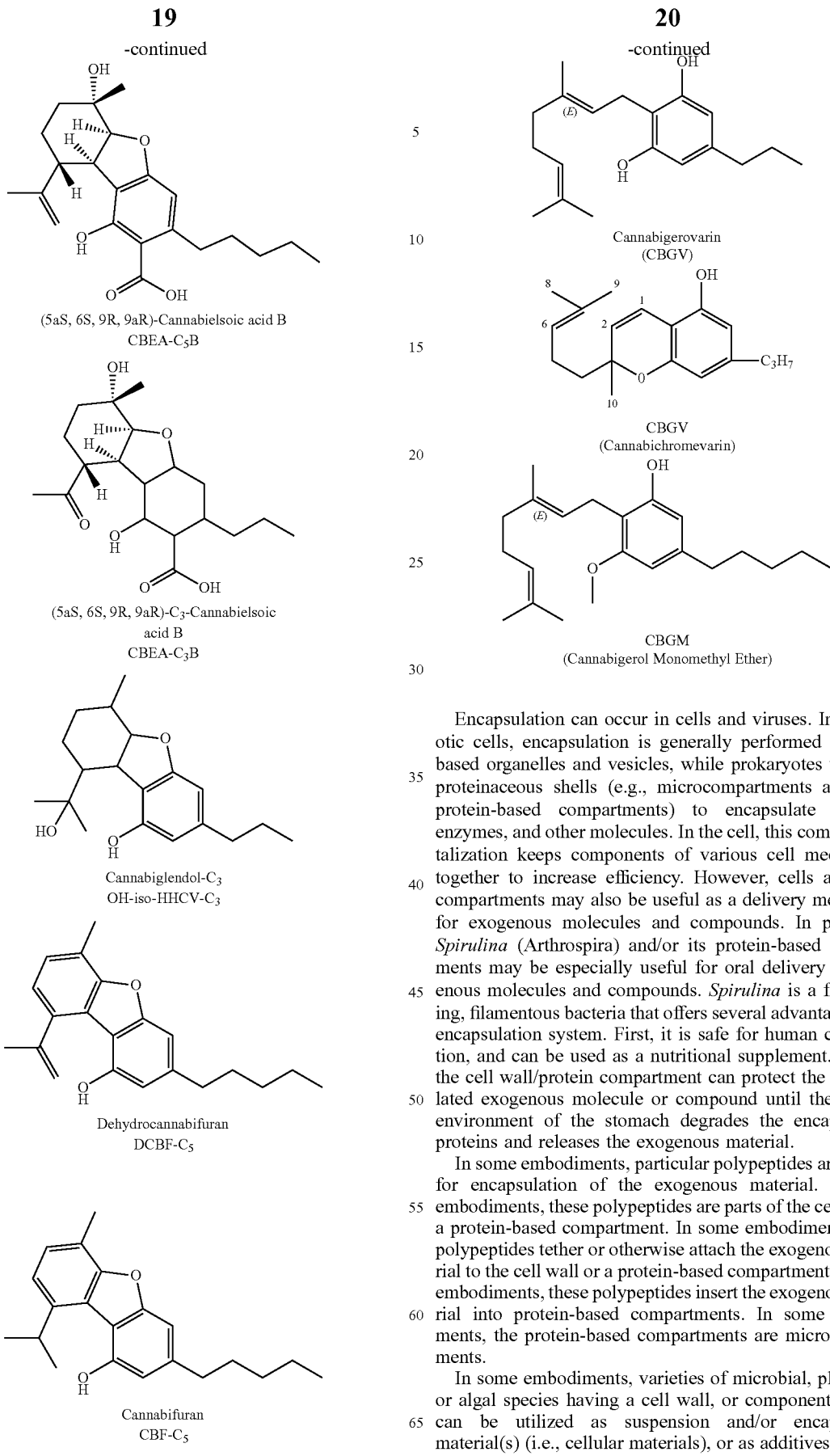

Encapsulation can occur in cells and viruses. In eukaryotic cells, encapsulation is generally performed by lipid-based organelles and vesicles, while prokaryotes use large proteinaceous shells (e.g., microcompartments and other protein-based compartments) to encapsulate proteins, enzymes, and other molecules. In the cell, this compartmentalization keeps components of various cell mechanisms together to increase efficiency. However, cells and these compartments may also be useful as a delivery mechanism for exogenous molecules and compounds. In particular, *Spirulina* (Arthrospira) and/or its protein-based compartments may be especially useful for oral delivery of exogenous molecules and compounds. *Spirulina* is a free-floating, filamentous bacteria that offers several advantages as an encapsulation system. First, it is safe for human consumption, and can be used as a nutritional supplement. Second, the cell wall/protein compartment can protect the encapsulated exogenous molecule or compound until the low-pH environment of the stomach degrades the encapsulating proteins and releases the exogenous material.

In some embodiments, particular polypeptides are needed for encapsulation of the exogenous material. In some embodiments, these polypeptides are parts of the cell wall or a protein-based compartment. In some embodiments, these polypeptides tether or otherwise attach the exogenous material to the cell wall or a protein-based compartment. In some embodiments, these polypeptides insert the exogenous material into protein-based compartments. In some embodiments, the protein-based compartments are microcompartments.

In some embodiments, varieties of microbial, plant, and/or algal species having a cell wall, or components thereof can be utilized as suspension and/or encapsulation material(s) (i.e., cellular materials), or as additives, and can include: Algal species such as *Dunaliella salina*, Haematococcus pluvialis, Coelastrella *striolata*, Diatoms such as *Phaeodactylum tricornutum*, and *Isochrysis galbana*, such as Cyanobacteria such as Arthrospira *platensis* and Arthrospira maxima; *Chlorella* species such as *Chlorella autotrophica, Chlorella colonials, Chlorella lewinii, Chlorella minutissima, Chlorella pituita, Chlorella pulchelloides, Chlorella pyrenoidosa, Chlorella rotunda, Chlorella singularis, Chlorella sorokiniana, Chlorella variabilis, Chlorella volutis, Chlorella vulgaris*; Macroalgae species, seaweed of the types: red, brown, and green such as *Porphyra* sp., Chondrus *crispus, Gigartina stellata*, G. radula, G. *acicularis*, G. pistillata, Eucheuma *spinosum, Polyides rotundus, Osmundea pinnatifida*, Pterocladiella capillacea, Sphaerococcus coronopifolius, and Gelidium microdon, Rhodophyta; Cystoseira *abies*-marina and Fucus *spiralis*, Phaeophyta; Ulva *compressa*, Chlorophyta; Kelp species such as Ascophyllum nodosum, Laminara *Digitata*; Other plants species such as aloe, alfalfa, turmeric root (*Curcuma longa*), ginger root, wheatgrass, and *Cocos nucifera*: Nutritional yeasts such as S. *cerevisiae*; Probiotic strains such as *Lactobacillus acidophilus, Lactobacillus plantarum, Lactobacillus gasseri, Lactobacillus paracasei, Lactobacillus bulgaricus, Lactobacillus brevis, Lactobacillus casei, Lactobacillus rhamnosus, Lactobacillus salivarius, Bifidobacterium lactis, Bifidobacterium bifidum, Bifidobacterium breve, Bifidobacterium infantis, Bifidobacterium longum*; and Species often used in Kombucha production such as species of the genus *Zygosaccharomyces, Acetobacter* and *Gluconacetobacter*.

In some embodiments, the cellular material used for encapsulation is *Spirulina* (e.g., Arthrospira *platensis*). *Spirulina* is an ecologically sound, nutrient-rich dietary supplement. Dried *Spirulina* often includes about 5% water, about 24% carbohydrates, about 8% fats, and about 51% to about 71% (e.g., about 60%) protein (amino acids), along with vitamins and minerals. More specifically, in some embodiments 100 grams (g.) of dried *Spirulina* has an energy of about 290 kcal, about 23.9 g. of carbohydrates (including about 3.1 g. of sugars and about 3.6 g. dietary fiber), about 7.72 g. of fat (including about 2.65 g. of saturated fat, about 0.675 g. of monounsaturated fat, and about 2.08 g. of polyunsaturated fat), and about 57.47 g. of protein (including about 0.929 g. of tryptophan, about 2.97 g. of threonine, about 3.209 g. of isoleucine, about 4.947 g. of leucine, about 3.025 g. of lysine, about 1.149 g. of methionine, about 0.662 g. of cystine, about 2.777 g. of phenylalanine, about 2.584 g. of tyrosine, about 3.512 g. of valine, about 4.147 g. of arginine, about 1.085 g. of histidine, about 4.515 g. of alanine, about 5.793 g. of aspartic acid, about 8.386 g. of glutamic acid, about 3.099 g. of glycine, about 2.382 g. of proline, and about 2.998 g. of serine), as well as various vitamins and minerals.

*Spirulina* used in methods of the present disclosure may be commercially available and/or artificially cultivated. Fresh *Spirulina* and/or dry *Spirulina* may be used, with fresh *Spirulina* being preferable in some embodiments since fresh *Spirulina* is enriched in nutrients of *Spirulina*.

*Spirulina* may be cultivated by any known method used in the cultivation of blue-green algae and, for example, viable *Spirulina* can be inoculated in a culture medium in a concentration of 20 to 500 mg/L based on the weight of the algal dry biomass, and then cultivated. A light source used in the cultivation may be sunlight or artificial light, for example a light source of 1,000 to 100,000 λx. The cultivation temperature can be from 20° C. to 65° C., for example from 30° C. to 40° C. The cultivation period can be from about 5 days to about 10 days. During the cultivation, an amount of carbonate ions in the solution can be increased by appropriately blowing a carbon dioxide gas or an air.

As used herein "*Spirulina*" can be synonymous with "Arthrospira." The genus Arthrospira includes at least 57 species of which 22 are currently taxonomically accepted. Thus, reference to "*Spirulina*" or "Arthrospira" without further designation can include reference to any of the following species: A. amethystine, A. ardissonei, A. argentina, A. balkrishnanii, A. baryana, A. boryana, A. *braunii*, A. *breviarticulata, A. brevis*, A. curta, A. desikacharyiensis, A. *funiformis, A. fusiformis*, A. ghannae, A. gigantean, A. *gomontiana, A. gomontiana* var. *crassa, A. indica*, A. jenneri var. *platensis*, A. jenneri Stizenberger, A. jenneri F. *purpurea*, A. joshii, A. khannae, A. *laxa, A. laxissima, A. laxissima*, A. leopoliensis, A. major, A. *margaritae, A. massartii, A. massartii* var. indica, A. maxima, A. meneghiniana, A. *miniata* var. *constricta, A. miniata, A. miniata* F. *acutissima*, A. neapolitana, A. *nordstedtii*, A. oceanica, A. *okensis*, A. pellucida, A. *platensis, A. platensis* var. non-*constricta, A. platensis* F. granulate, A. *platensis F. minor, A. platensis* var. *tenuis*, A. santannae, A. *setchellii*, A. skujae, A. *spirulinoides* F. *tenuis, A. spirulinoides, A. subsalsa, A. subtilissima, A. tenuis, A. tenuissima*, and A. *versicolor*.

Depending on the embodiment and/or implementation, a product or finished product according to the disclosure can take on any of a wide variety of forms, including but not limited to: flake, granule, shred, pellet, tablet, powder, stick, wafer, or sheet. Flake material, for example, can be configured to be high in Tetrahydrocannabinol-H ("THC-H") and/or have particular cannabinoid profiles. A finished product can be further modified or incorporated into a modified "end" product which can also take on any of a wide variety of forms, including (but not limited to): a baked good (e.g., a cookie, brownie, cake, etc.), a spice rub, a pastille, lozenge, gum, spread, oil, etc., and/or be configured as a product for buccal delivery, such as a lozenge or pastille, a snus-like product or pouch (e.g., woven or non-woven, and/or having a dissolvable pouch), etc. For a snus or snus-like application, since components of the finished product can have an adherent, or "sticky" texture, it can be desirable to employ a dissolvable pouch, such that the inner contents (i.e., the finished product) is eventually directly exposed to a mouth of a user, such that one or more components is delivered via buccal, sublingual, and/or oral administration.

In some implementations, products and/or finished products of the present disclosure are one or more of alcohol-free, substantially alcohol-free, essentially alcohol-free sugar-free, substantially sugar-free, essentially sugar-free (i.e., free from added sugar), gluten-free, substantially gluten-free, fat-free, or substantially fat-free. For example in some such implementations, the finished product is alcohol-free, sugar-free, gluten-free, and fat-free.

Turning to FIG. 1A, a process flow illustrating a method 100 for encapsulating a lipid/complex lipid mixture is shown. At 102A, an extract material (e.g., a *Cannabis* extract) is obtained. The extract material can include one or more of:

Shatter: a transparent *Cannabis* extract. Shatter is a highly stable concentrate that can be easily broken/shattered. Most shatters are transparent in color and can be handled without considerable residue. However, exposing shatter to heat, even room temperature, can cause shatter to become oil. If a concentrate is exposed to enough heat, it can decarboxylate permanently/irreversibly.

Crumble: a dry extract with a cheese-like structure that can be crumbled and is not transparent like shatter. Crumble is formed by agitating an oil until it reaches a point of crystallization, which removes its translucent color. Crumble is often stored using parchment paper.

Budder: has a consistency that is between wax and crumble. Budder is versatile for use both indoors and outdoors, and is often manipulated using a tool.

Oil e.g., butane hash oil ("BHO"): a kind of hash oil that is extracted from *Cannabis* through the use of butane. There are solid forms and oily forms of BHO. The BHO process extracts the cannabinoids, terpenes, waxes, concrete oils, and occasionally, chlorophyll, from the plant itself. After the BHO process, the butane is removed from the final product. The BHO process is often used for mass production.

e.g., propane hash oil ("PHO"): a kind of bash oil that is extracted from *Cannabis* through the use of propane. PHO can have a consistency similar to that of budder, because propane extraction processes use elevated pressures as compared with BHO, and thus can remove different ratios of oils and wax from the plants compared to the butane process. PHO can preserve more terpenes and remove residuals, depending on the *Cannabis* strain that you use.

Nug Run Concentrate: This form of extract can have more trichomes and terpenes than the *Cannabis* plant itself, making it rich in flavor and less harsh to smoke.

$CO_2$ Concentrate: This form of extract has a liquid amber or golden appearance, and is often used in cartridges used for vape pens. A benefit of using the $CO_2$ method is that it is safer than butane or propane extraction methods. In its final form, $CO_2$ oils do not include any harmful residual components, since the process itself is effective in killing any bacteria or mold that might have been present in the plant material. A disadvantage of $CO_2$ concentrate preparation methods is that its flavor profile is not as potent as BHO and PHO.

Rosin: Rosin extraction is not suitable for mass production, but it is safer than many other extraction methods. Rosin techniques often do not include the use of solvents.

Trim Run: This form of extract is made using *Cannabis* plant trimmings, and thus may be used to supplement other extraction techniques to reduce or eliminate waste of the *Cannabis* plant. However, trim run is often less potent than other concentrates/extracts, and can contain more chlorophyll than other extracts.

Live Resin: This form of extract is produced using frozen *Cannabis* instead of cured plant material. Dabbing live resin can preserve more terpenes and THC that the curing process usually removes. Live resin can have a more potent flavor and aroma, as compared with BHO produced using dried *Cannabis*. Several methods can effectively extract frozen buds, but the rosin technique is what gives you "Live Rosin," which has a better and more powerful flavor profile compared to other kinds of concentrates.

Sap: This form of extract is a sticky concentrate that is more suitable for use indoors or in lower-humidity conditions. Sap can be easier to handle than oils, but is often handled using tools, since manual handling easily cause melting of the sap.

Dry Sift: This form of extract is one of the finer forms of concentrates. Dry sift is made using silk screens in varying sizes, meshes and/or microns to isolate the trichome heads from the bud. The silk screens are used to ensure that only the finest form of material ends up in the final product. Dry sift can be a lower-yielding process than some other extraction techniques. Dry sift can have a desirable flavor profile since the dry sift production process is highly effective at preserving terpenes. Dry sift has a soft, sand-like consistency that is pourable.

Ice Water Hash: This form of extract is prepared using ice water extraction, and has a texture/consistency similar to that of dry sift. During ice water extraction, ice and water are used to agitate the trichome heads off the *Cannabis* plant. Ice water hash can be made by hand or with the use of a washing machine, after which a filter can be used to separate the material and water using screens with different microns or meshes. The screens are used, for example, to prevent any unwanted particles from ending up in the final product because they isolate the glandular trichome heads. A metal strainer can be used to break down the hash so that it can be cured once all moisture has been removed. The ice water hash can then be stored in an air-tight glass container for curing.

Full Melt: This form of extremely high-quality/purity extract can be made using either the dry sift or ice water hash method. In full melt concentrate, no plant material at all is included in the end product. Full melt is often made using only, or substantially only, isolated trichome heads (e.g., with no residual components). Full melt is susceptible to melting at slight/low exposure to heat Wax: This form of extract has a form that is between a solid and liquid, can have an earwax appearance, and is relatively easily manipulable (often with tools).

Pull and Snap: This form of extract is a moderately stable, solid form of *Cannabis* concentrate. Pull and snap is flexible, and can be bent or rolled (e.g., into ball form). Pull and snap is suitable for outdoor use, and is often stored in a non-stick container.

Fraction

THC

CBD

Any other product resulting from an extraction or hydraulic press operation applied to a plant.

The extract material can include a predetermined amount of cannabinoids (e.g., about 40% to about 99% cannabinoids, or about 55% to about 90% cannabinoids, or about 70% to about 90% cannabinoids). Although FIG. 1A shows obtaining an already-prepared extract material, optionally, prior to beginning the method 100, *Cannabis* material (e.g., *Cannabis* plant trim and/or flower) can be obtained and an extraction thereof is prepared using one or more extraction methods, including (but not limited to): solvent extraction (e.g., butane extraction, ethanol extraction, or low-grade alcohol extraction, supercritical carbon dioxide ($CO_2$) extraction, olive oil extraction, etc.), a rosin or resin extraction, a "press" extraction, etc. At 102B, the extract material can optionally be decarboxylated. Once decabroxylated, the extract material can have a honey-like, adherent or adhesive-like (i.e., "sticky") consistency.

Separately, at 102C (e.g., at a different time, the same time, concurrently, or substantially concurrently), a polar liquid (such as an aqueous solution, a water solution, water (for purposes of illustration and not limitation, distilled water) is obtained, and a pH of the distilled water is increased ("up-adjusted), at 102D, for example to a pH of about 9 to about 10, resulting in a "high pH water." The pH adjustment can be accomplished, for example, by adding sodium hydroxide (NaOH), a bicarbonate, and/or other food-safe pH-adjusting additive. Separately, at 102E (e.g., at a different time, the same time, concurrently, or substantially concurrently), *Spirulina* is obtained. The *Spirulina* and the high pH water are combined, at 102F, into an aqueous *Spirulina* solution (e.g., to about 3% weight of *Spirulina* per volume, or about 5% weight per volume, or about 7% weight per volume, or from about 0.5% to about 30% weight per volume, or from about 1% to about 9% weight per volume, or from about 1% to about 10% weight per volume, or from about 2% to about 4% weight per volume, or from about 3% to about 5% weight per volume, or from about 3% to about 7% weight per volume).

*Spirulina* can be found in nature, particularly in alkaline lakes. *Spirulina* as utilized herein can, according to some embodiments, be cultured/maintained at alkaline pH levels. In some embodiments, the pH of the aqueous *Spirulina* solution is alkaline (pH greater than 7). In some embodiments, the pH of the aqueous *Spirulina* solution is between about 8.5 and about 11. In some embodiments, the pH of the aqueous *Spirulina* solution is between about 9 and about 10.

Subsequent to the formation of the aqueous *Spirulina* solution, the aqueous *Spirulina* solution is processed to liberate (e.g., by disrupting the membrane) the cell contents of the *Spirulina* (e.g., to liberate the contents, including protein contents, of the *Spirulina* cells) while maintaining a relatively low temperature (e.g., at a temperature of about 69° C. or lower, or at room temperature or below, where "room temperature" refers to a temperature of between about 15° C. (59° F.) to about 25° C. (77° F.)). For example, the processing of the *Spirulina* can be performed in an ice bath. In some embodiments, the temperature is regulated to prevent denaturing of one or more cell contents, such as one or more proteins. First, at 102G, the *Spirulina* solution is blended or mixed. Such blending can be performed, for example, using an immersion blender (e.g., a hand immersion blender), mixer, or the like, either continuously or periodically (e.g., for about 30 seconds or for a series of 30-second durations with waiting periods in between to avoid excessive temperature increase), via agitation (e.g., using a stir rod or stir bead), sonication (e.g., low-frequency sonication at about 500 Hz), ultrasonication, etc., in some embodiments, while the temperature is monitored and/or regulated.

The aqueous *Spirulina* solution may be disrupted using any appropriate process, including mechanical or/or non-mechanical methods or processes. Methods of disrupting the cellular material include, but are not limited to lysis, acid hydrolysis, desiccation, enzymatic treatment, use of detergents, solvents, or antibiotics, physical means (e.g., osmotic shock, pressure) to solid shear, use of a bead mill, cell press (e.g., French press), liquid shear, ultrasonication, sonication, high-pressure homogenizer(s), ultrafine shearing, alkaline pretreatment, acidic pretreatment, homogenization, high-pressure homogenization, thermal, hydrothermal, pulsed-electric field, microwave-assisted extraction, or a combination thereof. In some embodiments, mechanical disruption of the cells may be preferable to chemical disruption as it can reduce or prevent chemical contamination while preserving (or substantially preserving) the functionality of the cell contents.

Next, at 102H, the aqueous *Spirulina* solution is ultra-sonicated (e.g., at greater than about 20 kHz, for example about 40 kHz) for a predetermined duration (e.g., about 30 minutes). This ultrasonication step (at 102H) can be referred to as a "first disruption," in that at least a portion of the *Spirulina* proteins are liberated. As used herein, a "disruption" can refer to an at least partial liberation of proteins of the *Spirulina* or other cellular encapsulant material. In some implementations, the aqueous *Spirulina* solution can be cooled (e.g., by adding ice, refrigerating, etc.) during one or both of 102G and 102H.

The disruptions of method 100 may be performed for any of a variety of durations, depending upon the implementation. For example, in some embodiments, the disruptions are performed for durations sufficient (either individually or collectively) to liberate the components, such as proteins, desired or needed for encapsulation. Liberation of proteins and/or other components from the *Spirulina* cell can be measured by any of a variety of mechanisms or methods appropriate for a particular application according to the disclosure. For example, the amount of proteins in solution can be measured by determining the absorbance of the solution at 280 nm; as whole cells are disrupted, this absorbance measurement should increase. Alternatively, or additionally, protein concentration can be measured by methods including but not limited to: Bradford assay, colorimetric assays, biuret test, Lowry protein assay, and bicinchoninic acid assay (BCA).

At 102I, the extract material (optionally decarboxylated) and the aqueous *Spirulina* solution are combined in a predetermined ratio to form an "intermediate mix." In some implementations, the extract material and the *Spirulina* solution are combined shortly or immediately after the extract material is removed from a decarboxylation oven, while the extract material is still warm and flowable, e.g., for improved incorporation of the extract material into the aqueous *Spirulina* solution. Alternatively and/or additionally, the aqueous *Spirulina* solution can be heated while being combined with the extract material, however in such cases the heating can be monitored and/or regulated, and/or controlled such that it is applied for limited duration (e.g., at a temperature of about 69° C. or lower and/or for a duration of not more than 3 hours) to avoid unwanted microbial growth. It should be noted that the temperatures and times discussed herein can be varied based on the particular implementation, and any number of applicable factors, such as ambient humidity, controlled environment, pressure, etc. In some embodiments, the extract material is added to the aqueous *Spirulina* solution, while in other embodiments, the aqueous *Spirulina* solution is added to the extract material.

The predetermined ratio of extract material to *Spirulina* solution can be, for example, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10 (weight: weight). At 102J, the intermediate mix undergoes a "second disruption," during which encapsulation/stabilization occurs, and which is performed via one or both of cold ultrasonication (102K) or heated ultrasonication (102L). As shown in FIG. 1A, cold ultrasonication 102K can be performed for a predetermined duration (e.g., about 2 hours) and/or at a predetermined temperature (e.g., room temperature or below). By contrast, heated ultrasonication can be performed for a predetermined duration (e.g., about 45 minutes) and/or at a predetermined temperature (e.g., about 69° C.). In some cases, heated ultrasonication is performed for a shorter duration than cold ultrasonication, for example to mitigate microbial growth. In some implementations, the intermediate mix only undergoes one of cold ultrasonication 102K or heated ultrasonication 102L as part of the encapsulation step 102J. In other implementations, the intermediate mix only undergoes both at least one cold ultrasonication 102K and at least one heated ultrasonication 102L, in any order, as part of the encapsulation step 102J. As a result of the second disruption/encapsulation step 102J, a "fully disrupted, encapsulated mixture" is produced, in which all or substantially all of the *Spirulina* proteins have been liberated, and in which all or substantially all of the extract material is encapsulated by the *Spirulina* solution.

At 102M, a pH of the fully disrupted, encapsulated/stabilized mixture is optionally reduced (e.g., to a pH of about 7, about 6.5, about 6, about 5.5, about 5, about 4.5, about 4, about 3.5, about 3, or about 2.5), for example by adding an acid, such as citric acid, ascorbic acid, phosphoric acid, tartaric acid, lactic acid, a combination of citric acid and ascorbic acid, any other food grade acid or combinations thereof, or one or more salts thereto. Addition of a pH-adjusting additive (e.g., citric acid) can have one or more benefits, including: mitigation of microbial growth in the finished product, enhancement to salivary response, improved taste, action as a masking agent, increase buccal and/or sublingual absorbance/uptake, etc.

At 102N, the encapsulated mixture (e.g., in the form of a slurry) is poured onto a substrate to form a layer or film, for example such that the poured layer has a predetermined volume per unit area (e.g., about 2.5 mL per square inch of substrate area, or from about 1 mL to about 5 mL, or about 7 mL, or about 8 mL, or about 10 mL, or about 12 mL, or about 14 mL, or about 16 mL, or about 18 mL, or about 18 mL-22 mL, or about 20 mL, or about 22 mL per square inch of substrate area). The substrate can be a glass, a coated surface (e.g., TEFLON-coated, etc.), silicone, or other substrate/non-stick substrate. At 102P, the poured mixture is dehydrated at a predetermined temperature (e.g., about 165° F.) for a predetermined duration (e.g., about 15 hours or longer, from about 1 minute to about 10 days, about 1 minute to about 60 minutes, about 1 hour to about 10 hours, about 2 hours to about 5 hours, about 5 hours to about 10 hours, about 10 hours to about 20 hours, about 15 hours to about one day, about 1 day to about 5 days, or about 5 days to about 10 days), and optionally in a predetermined environment (e.g., ambient conditions, low-humidity conditions, nitrogen-filled drybox conditions, vacuum conditions, etc.) to produce a final/finished product. Alternatively to steps 102N and 102P, one or more other drying techniques 102Q (e.g., disposition on salt or sugar, desiccation, lyophilization, nano-spray drying, etc.) can be performed on the fully disrupted, encapsulated mixture. The finished product, when prepared using drying steps 102N and 102P, and once removed from the silicone substrate, can have a flat, flake-like texture similar to flake-type fish food. The flake-like finished product can be configured to not fully dissolve in water, and instead may dissociate. For example, in some embodiments, when exposed to an aqueous environment (e.g., sublingual, buccal, or oral environment), the flakes or other product can be configured to disperse into particles having an average size from between about 0.5 mm to about 1 nm. In some implementations, the flakes can be graded (e.g., as small, medium, or large size) and sorted for use in a variety of applications. Alternatively, the flakes can be ground, milled or otherwise further mechanically processed, for example to generate a powder for subsequent use in a variety of applications.

In some implementations of method 100, no step is performed at or above a temperature that promotes microbial growth, and/or such that mean temperature (and/or other environmental parameters) are maintained to avoid or substantially avoid conditions that allow or promote undesired or harmful microbial growth.

In some implementations of method 100, a sterilization step can be performed, e.g., to the finished product and/or to the *Spirulina* (e.g., prior to step 102F). Sterilization can be performed, for example, using ultraviolet (UV) sterilization, proton sterilization, microwave sterilization, etc., for example to remove bacterial contamination, fungal contamination, viral contamination, and/or the like. Alternatively or in addition, sterilization can be performed by drying (102P or 102Q) at an elevated temperature (e.g., about 150° F., about 155° F. to about 165° F., about 165° F., about 150° F. or higher, about 150° F. to about 170° F., about 100° F. to about 200° F., etc.) and/or at pressures and/or in conditions that reduce or neutralize one or more dangerous contaminants.

In some implementations of method 100, dehydration at 102P, when performed on the disrupted, encapsulated mixture without a pH reduction at 102M, can result in a modified consistency (e.g., a non-flake form) of the finished product. Without the pH reduction at 102M, a flake-like consistency can still be obtained, for example, by adding a salt or other metabolite (e.g., prior to drying).

In some implementations of method 100, the finished product is partially dissolvable in water or another solvent. For example, when placed in water, the finished product may be about 20% insoluble, about 19% insoluble, about 18% insoluble, about 17% insoluble, about 16% insoluble, about 15% insoluble, about 14% insoluble, about 13% insoluble, about 12% insoluble, about 11% insoluble, about 10% insoluble, about 9% insoluble, about 8% insoluble, about 7% insoluble, about 6% insoluble, about 5% insoluble, about 4% insoluble, about 3% insoluble, about 2% insoluble, or about 1% insoluble.

In some implementations of method 100, one or more parameters can be modified such that less than all of the extract material is encapsulated by the *Spirulina* solution. In such implementations, the finished product can be more fully dissolvable in water than the unmodified method 100.

As used herein, a "*Spirulina* solution" can refer to a solution that includes one or more components (e.g., proteins, waxes, etc.) derived from *Spirulina*, and does not necessarily require that all parts of the original whole cell *Spirulina* are retained in the solution.

In some embodiments, one or more additives can be added, at one or more steps of the method 100 and/or can be added to the finished product. For example, a powder or oil additive may be introduced prior to encapsulation. Alternatively or in addition, an oil can be added before pouring, following an agitation step (e.g., to avoid encapsulation of the flavorant). Additives can include, but are not limited to: vitamins, minerals, supplements, flavorants (e.g., peppermint oil, menthol, cinnamon, lime and lemon extract, pomegranate extract, chili oil etc.), relaxants (e.g., magnesium, zinc, melatonin, chamomile, etc.), and/or colorants.

Finished products produced by the methods set forth herein can be used standalone (e.g., as an additive for cooking, as a raw consumable, such as an edible, inhalable, or smokable, etc.) or incorporated into (e.g., used as an ingredient in) another product (e.g., oil-based infusions, inhalers/vaporizers, baked goods, beverages, etc.). Finished products can be configured for administration via one or more pathways, including but not limited to mucosal membranes, via insufflation, inhalation, buccal administration, sublingual administration, etc. Example finished product, prepared according to the method 100 of FIG. 1A, exhibited surprising properties evidencing the success of the encapsulation/stabilization process. For example, despite the addition of citric acid at step 102M, in one embodiment, the finished product showed no degradation of THC after an aging period. Moreover, example finished product prepared according to the method 100 of FIG. 1A were "water tested" in a cold, dark environment for 30 days by adding the finished product to water and a xanthan gum stabilizer, and no degradation was observed. In some embodiments, the finished product has a shelf life (i.e., where the active does not degrade more than 10%) of at least about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, or about 1 year.

In some implementations of the method 100, a granulation can be performed after the decarboxylation 102B and before the combination 102I. As used herein, "granulation" refers to breaking down into smaller pieces, particles, particulates or components, for example by cutting, grinding, agitating, blending, chopping, pulverizing, etc.

Any strain of *Cannabis* (e.g., Black Jack, Gelato, Gorilla Glue #4 ("GG4"), Lemon Garlic OG, Sour Diesel, Sunset Sherbet, etc.) can be used to prepare the extract material for use in a process of the present disclosure. Black Jack *Cannabis* is grown in organic soil, has a 9-week flower cycle, and produces dense buds with a grape-like structure, often covered in THC-filled trichomes. The Black Jack flavor profile begins with an earthy citrus flavor and finishes with a sweet and peppery flavor. The GG4 flavor profile includes a sweet pine finish, earthy aromas and a distinct pungent note. Sour Diesel is a *Sativa*-dominant strain with a citrus and diesel fuel aroma profile, and can be used to relieve anxiety, depression, and/or chronic fatigue. Lemon Garlic OG is a 20% *Sativa*/80% Indica d grown from feminized seeds. Lemon Garlic OG often includes low levels of CBD and from 8-20% THC, and is an aromatic strain with citrus, pine and garlic flavors. in some embodiments, the genetic profile of *Cannabis*, when used to prepare the extract material for use in a process of the present disclosure, can influence the potency, flavor and/or other attributes of the finished product.

In some cases, adjustments to the ratio of extract material to *Spirulina* solution to form the "intermediate mix" (e.g., at 102I of FIG. 1A) can impact the potency (e.g., of the THC, CBD, and/or other active/psychoactive constituents of the extract material encapsulated therein), as well as the physical properties (e.g., texture, color, surface area, surface roughness, solubility, tensile strength, hardness, volume per weight, optical transparency or translucency, pore size, etc.) of the finished product. For example, in some embodiments, increasing the proportion of *Spirulina* solution can result in a less flaky finished product, resembling dried seaweed. By contrast, reducing the proportion of *Spirulina* solution can result in a finished product having a yellowish, highly brittle film in which not all of the extract material is encapsulated (i.e., the extract material is less than fully encapsulated).

In some cases, the thickness of the poured encapsulated mixture at 102N affects the consistency of the finished product. For example, depending on the implementation, a larger thickness (or deeper pour) can result in a more relatively more flexible, ductile, brittle, resilient, flaky, firm, and/or elastic (i.e., stretchable) finished product (depending on the other materials and processes utilized). For example, where a larger thickness results in a more flexible product for a particular implementation, a relatively smaller thickness can lead to a more brittle finished product. An excessively thick pour may result in a cracker-like product.

Since the method of FIG. 1A uses a whole cell microorganism (rather than a single molecule constituent or other subdivision component of the whole cell microorganism) to encapsulate a lipid, there is no need to isolate such components, and the method can be faster and more efficient than known encapsulation methods.

Figure 1B:
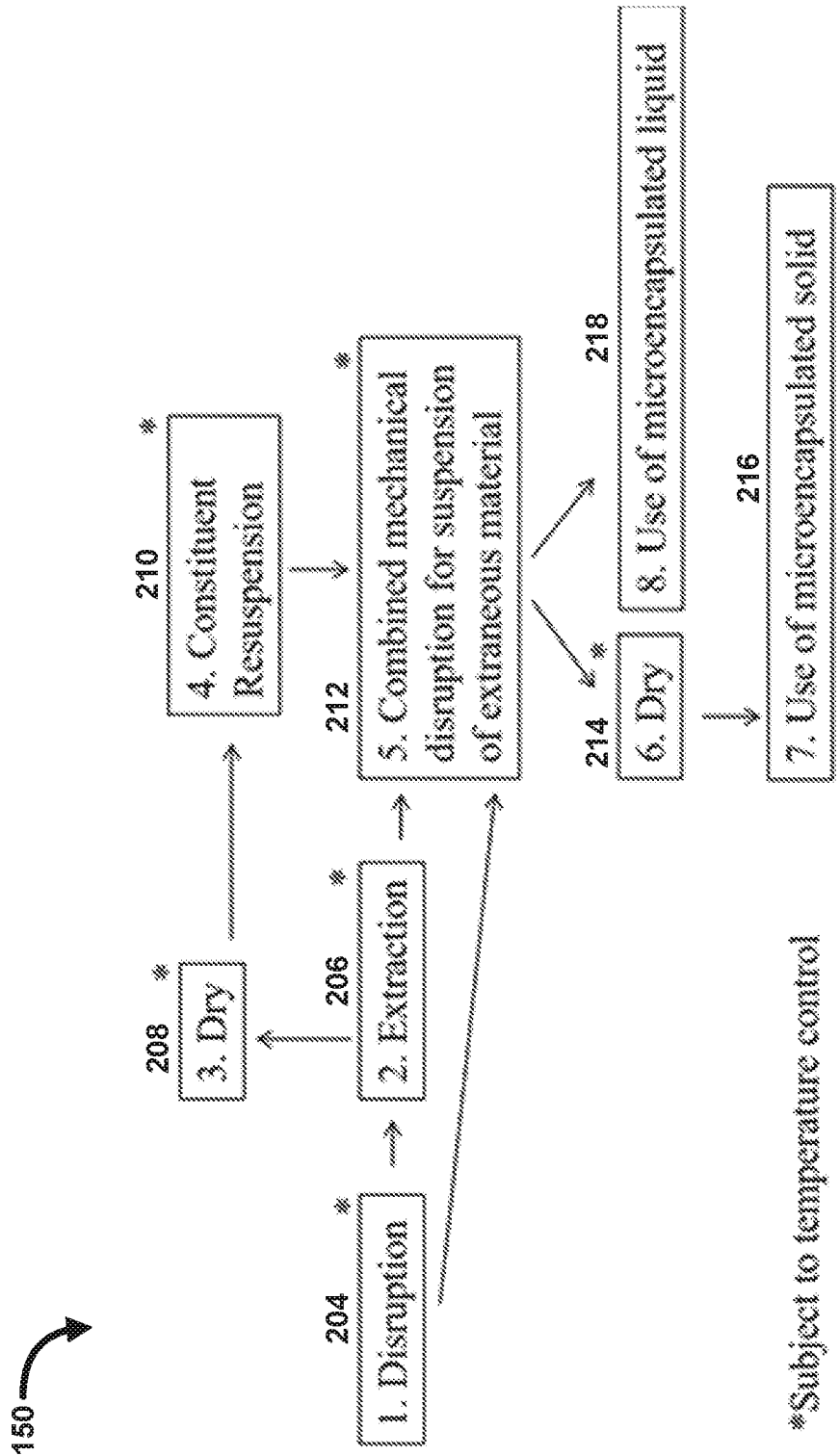
FIG. 1B is a tree diagram illustrating methods for encapsulation of an extract material, according to some embodiments.

FIG. 1B is a tree diagram 150 illustrating methods for encapsulation of an extract material, according to some embodiments. As shown in FIG. 1B, the method includes the following steps: disruption of an aqueous solution (e.g., an aqueous solution containing cellular material, such as *Spirulina*, in a solvent) 204, extraction of constituent materials from the cellular materials 206, drying steps 208 and 214, constituent resolubilization/resuspension 210, combined mechanical disruption 212, use of a microencapsulated solid 216, and use of a microencapsulated liquid 218. Each of disruption 204, extraction 206, drying steps 208 and 214, constituent resuspension 210, and combined mechanical disruption 212, as indicated by asterisks in FIG. 1B, can be subjected to temperature control (e.g., heating or cooling). Each of the microencapsulated liquid and the microencapsulated solid can be referred to as a finished product. As shown in FIG. 1B, there are multiple possible paths through the diagram (i.e., multiple different methods are represented), as indicated by arrows.

In a first method of the tree diagram 150, a first disruption 204 is immediately followed by a combined mechanical disruption 212, for suspension of extraneous material and the formation of a microencapsulated liquid. Subsequent to the combined mechanical disruption 212, the microencapsulated liquid is either used, at 218, or dried at 214 to form a microencapsulated solid, which can then be used at 216.

In a second method of the tree diagram 150, a first disruption 204 is immediately followed by an extraction 206 before the combined mechanical disruption 212 for suspension of extraneous material and the formation of a microencapsulated liquid. As in the first method, subsequent to the combined mechanical disruption 212, the microencapsulated liquid is either used, at 218, or dried at 214 to form a microencapsulated solid, which can then be used at 216.

In a third method of the tree diagram 150, a first disruption 204 is immediately followed by an extraction 206, a first drying step 208, and a constituent resuspension 210 before the combined mechanical disruption 212 for suspension of extraneous material and the formation of a microencapsulated liquid. As in the first method, subsequent to the combined mechanical disruption 212, the microencapsulated liquid is either used, at 218, or dried at 214 to form a microencapsulated solid, which can then be used at 216.

In some implementations of a method of tree diagram 150, when water or another polar solvent is used as the solvent, the water may be pH-adjusted, e.g., according to a predetermined timing. In some such embodiments, the pH of the water is adjusted prior to cellular disruption (i.e., before 204), after cellular disruption (after 204), during the extraction process (206), during the constituent resuspension (210), during the combined disruption (212), or prior to the drying at 214.

The pH may be adjusted to a value of from about 7 to about 10, at concentrations ranging from about 0.5 mM to about 50 mM, using a pH-adjusting agent or compound, such as ammonium aluminum sulphate, ammonium bicarbonate, ammonium carbonate, ammonium hydroxide, ammonium phosphate di basic and ammonium phosphate mono basic, magnesium carbonate, magnesium hydroxide, sodium carbonate, sodium bicarbonate, potassium carbonate, potassium bicarbonate, sodium hydroxide, and/or calcium hydroxide.

Alternatively or in addition, pH-modification of the aqueous solution may be carried out by pH modifying compounds citric acid, acetic acid, amino acids such as glutamate, glycine, ascorbic acid, sodium hydroxide, tartaric acid, malic acid, fumaric acid, and lactic acid, When water is the solvent, osmolarity may be adjusted by the use of one or more salts and/or buffers, for example sodium chloride (NaCl) or magnesium sulfate ($MgSO_4$), at a concentration ranging from 0 mM to 500 mM.

In some embodiments where the final product is a liquid, the amount of polar solvent in the final microencapsulated liquid ("concentrate") can range from about 15% to about 99.9%, or about 50% to about 99.9%, or about 55% to about 95%, or about 60% to about 90%, or about 65% to about 85%, or about 70% to about 80%, or about 75% to about 99.9%, or about 75% to about 90%, or about 70% to about 90%, or about 60% to about 80%, or about 50% to about 80%, or about 90% to about 99.9%, or about 60% to about 80%, or about 95% to about 99.9%, or about 50% to about 70%, or about 50% to about 80%.

In some embodiments, variations of hydrophobic compounds, in the form of an oil or a wax, can include one or more terpenes, sterols, lipids, antioxidants, cannabinoids, and/or other compounds of medicinal and/or nutraceutical value. Examples of terpenes included in microencapsulated material include borneol, carophyllene, cineole, delta-3-Carene, limonene, linalool, myrcene, pinene, pulegone, and/or terpineol. Examples of classes of plant sterols that may be included in the encapsulated material are type sterol esters, sterols, and pro-sterols. Examples of lipids that may be included in the encapsulated material include α-linolenic acid, arachidonic acid, eicosapentaenoic acid, and docosahexaenoic acid. Examples of antioxidants that may be included in the encapsulated material include zeaxanthin, lutein, α-carotene, fucoxanthin astaxanthin, canthaxanthin, and β-carotene. Examples of cannabinoids that may be included in the encapsulated material include Cannabigerol (CBG), Cannabichromene (CBC), Cannabicyclol (CBL), Cannabivarin (CBV), Tetrahydrocannabivarin (THCV), Cannabidivarin (CBDV), Cannabichromevarin (CBCV), Cannabigerovarin (CBGV), Cannabigerol Monomethyl Ether (CBGM), Tetrahydrocannabinol (THC), Tetrahydrocannabinolic acid (THCA), Cannabidiol (CBD), Cannabidiolic Acid (CBDA).

Example non-polar, hydrophobic additives to the oil/wax include fatty acids such as omega-3 fatty acids, eicosapentaenoic acid (EPA), docosahexaenoic acid (DHA), alpha-Linolenic acid (α-Linolenic acid; ALA), conjugated linoleic acid and oils containing fatty acids such as fish oil, algae oil, krill oil, flaxseed oil, soybean oil, and walnut oil.

Example additives to the oil/wax include compounds containing and contained in fatty acids such for example, triglycerides, including, polar lipids, for example, phosphoric acid, choline, fatty acid chains, glycerol, glycolipids, triglycerides, fatty acid esters, and phospholipids (e.g., phosphatidylcholine, phosphatidylethanolamine, and phosphatidylinositol).

Alternatively or in addition, example additives to the oil/wax are compounds containing fat-soluble vitamins, for example, Vitamins D, E, K, and A, corresponding provitamins and vitamin derivatives such as esters. Additionally, water-soluble vitamins, made lipid soluble may also be included. For example, ascorbyl palmitate, a fat-soluble version of vitamin C.

Example non-polar additives to the oil/wax include compounds containing carotenoids such as beta carotene, mixed carotenoids (mixtures of alpha and beta), zeaxanthin, capsanthin, canthaxanthin, bixin lycopene, violerythrin, gamma carotene, astaxanthin, and lutein.

In some embodiments, herbs and/or spices (e.g., curcumin) may be added to wax/oil, such that they may be microencapsulated with the concentrate, or added to the aqueous solution.

Example additives to the "concentrate" (i.e., the finished products) include compounds containing micronutrients, such as vitamins, minerals, co-factors, and extracts such as coenzymeQ10, curcuminoids (turmeric extract), ginger extract, niagen, trimethylglycine, inositol, choline, citicoline N-acetyl-cysteine, astaxanthan, saffron, marigold, magnesium, zinc, melatonin, *ginseng* extract, glutamate, niacin, b vitamins, folic acid, vitamin b12, taurine, glucaronic acid, malic acid, and n-acetyl-tyrosine.

Examples of stabilizers that may be added to the concentrate (i.e., the finished products), for example to improve "mouthfeel" and/or to modify a property thereof (e.g., to increase the density and/or viscosity of the concentrate) include guar gum, xanthan gum, gum acacia, sodium alginate, carrageenan, Saladizer®, and marine red-algae.

In some embodiments, one or more preservatives, such as EDTA, citric acid, acetic acid, sodium benzoate, sodium propionate, potassium sorbate, or sulphur dioxide, may be added to the concentrate or to one or both of the oil/wax material and the aqueous solution.

In some embodiments, cellular materials, importantly cellular wall and cellular membrane, may be broken, or "disrupted" (e.g., at 204 and/or 212) through use of mechanical disruption instrumentation such as a high pressure homogenizer, sonication (e.g., using a bath sonicator or a horn sonicator), Dounce homogenization, French press, and vigorous shaking with glass beads, paddle blenders, and industrial blending. A combination of these cellular rupturing techniques may be used to optimize cell disruption and to decrease the size of cellular debris.

In some embodiments, disruption of cellular materials (at 204 and/or 212) is performed via ultrasonication at a frequency ranging from about 15 kHz to about 75 kHz, and at a power of about 120 W or about 250 W. Filtration or centrifugation may be used after cellular disruption, for example to remove unwanted cellular debris.

Microencapsulation of extraneous hydrophobic material (at 212) may be performed before, during, and/or after the breaking/disruption of cellular wall/membrane material (204).

In some embodiments, extraction (at 206) of constituent materials from the cellular materials after mechanical disruption via solvent extraction (e.g., using ethanol, methanol, hexanes, ethy-lacetate, chloroform, other solvents, and/or mixtures of any of the foregoing), followed by drying (at 208) of the extracted material, and resolubilization (at 210) in water or another polar solvent.

In some embodiments, extraction of constituent materials from the cellular materials (206) after mechanical disruption (204), is followed by removal of unwanted cellular debris via a reduction in pH levels ranging from 3-5, removal of the supernatant, resuspension of the precipitate in a solvent having a pH ranging from 5-10, and drying of the precipitate (208). After drying (208), the material may be resolubilized (at 210) into an aqueous solution having a pH of from 3-9. Precipitation of the material is optional.

Resolubilization (at 210) of extracted cellular constituents may include one or more mixing, shaking, sonication, vortexing, and use of stabilizers such as glycerol, guar gum, xanthan gum, locust bean gum, acacia gum, karaya gum, and tara gum.

In some embodiments, the cellular material includes whole cells, and one or more constituents thereof are left unextracted. In such embodiments, natural flocculation or aggregation of cellular material and encapsulation of a dense oil/wax material may lead to settling. Reduction of coalescence can be abated by the addition of sulfuric acid, phosphoric acid, EDTA, and/or another chelating agent. Alternatively or in addition, cellular aggregation can be reduced by increasing the density of the solution using one or more salts, sugars, gums, or stabilizers.

In some embodiments, no extraction of the constituent cellular material is performed, and the cellular material is directly used as a microencapsulant for a suspension of extraneous hydrophobic material (i.e., extract material) though use of mechanical cellular disruption at concentrations of cellular material ranging from about 0.1 g/100 ml (0.1% (w/v)) to about 10 g/100 ml (10% (w/v)) for maximal disruption of the cellular material.

Depending upon the application, a selected ratio (e.g., at 212) of micro-encapsulated extraneous hydrophobic material (in grams) to dry cell weight (in grams) of cellular material (whether extracted or not extracted) can range from about 0.001 to about 1 (w/w) for optimal microencapsulation of the extraneous material. A selected ratio of compound to cellular material or extracted cellular material can depend on the type and characteristics of the extraneous hydrophobic material (extract material) to be encapsulated.

In some embodiments, pre-heating, simultaneous heating and/or post-heating of cellular material is performed via a method such as gravimetric convection heating or water bath heating, before, during and/or after one or more cellular disruption mechanisms are implemented. This heating may range from about 30° C. to about 100° C. (e.g., about 50° C.). A selected heating temperature or temperature range can vary according to the type of cellular material, its recalcitrance, lipid, protein, cell wall type, content, and/or concentrations.

In some embodiments, cooling of the cellular material before, during, and after the mechanical disruption process is performed, for example to a temperature ranging from about −20° C. to about 15° C., to preserve protein structures that stabilize cellular membrane and lipid structures.

In some embodiments, the polar solvent is altered before, during and/or after mechanical disruption of the material via addition of compounds, e.g., citric acid, acetic acid, trehalose, various polymeric gums, amino acids such a glutamate, glycerol, ethylenediaminetetraacetic acid ("EDTA"), phosphoric acid, ascorbic acid, sodium hydroxide, tartaric acid, malic acid fumaric acid, and lactic acid which alter pH, oxidation state, osmolarity, activity, or viscosity.

In some embodiments, mechanical cellular disruption is performed using a method that can depend on the type of cellular material being disrupted. Variations in lipid, protein, and cell wall content and type, as well as general recalcitrance, can influence the type and time of mechanical disruption. The time for mechanical disruption can range from about 5 minutes to about 180 minutes, or about 5 minutes to about 180 minutes, or about 1 hour to about 3 hours, or about 5 minutes to about 15 minutes, or about 10 minutes to about 25 minutes, or about 20 minutes to about 30 minutes, or about 30 minutes to about 45 minutes, or about 60 minutes to about 90 minutes, or about 60 minutes to about 120 minutes, or about 90 minutes to about 120 minutes, or about 2 hours to about 3 hours, or about 150 minutes to about 180 minutes. Reducing disruption time can help to maintain the integrity of the cellular material, whereas increasing disruption time can break/disrupt the cellular material while still allowing for micro-encapsulation of the extraneous, hydrophobic (extract) material.

In some embodiments, preparation of the extraneous, hydrophobic (extract) material to be microencapsulated includes heating of the extraneous, hydrophobic (extract) material at a predetermined temperature and for a predetermined duration. For example, the extraneous compounds may undergo changes in physical form, e.g., from solid to liquid, or from liquid to gas, to facilitate complete or substantially complete microencapsulation. Extraneous compounds may undergo structural changes catalyzed by heat, e.g., decarboxylation to improve encapsulation efficiency. The temperatures for altering the extraneous compounds can range from about 50° C. to about 270° C., and the heating duration for altering extraneous compounds can range from about 0 min. to about 120 min.

In some embodiments, alteration of the microencapsulation is performed through the addition of one or more emulsifiers, polymers, and/or sugars, for example to form gels, jelly-like compounds, or gummy materials.

Microencapsulated extraneous material (i.e., finished product) can be packaged and consumed "as-is," or as an addition/ingredient (e.g., in liquid or powder form) to one or more other consumable materials.

After microencapsulation of the extraneous material, the suspension can be dried to produce a solid form of microencapsulated material. The drying process may be carried out via one or methods such as, but not limited to: dehydration using vacuum, e.g., at a temperature ranging from about 10° C. to about 100° C., laminar air flow, e.g., at a Incorporation of the microencapsulated extraneous compounds (in both liquid and solid from) into dry goods such as cereals, grains, cakes, confections, spices, salts, seasonings for edible and medicinal consumption is included in one embodiment of the method. Additionally, the microencapsulated extraneous compounds (in either liquid or solid form) may also be consumed as-is, in concentrate form or diluted with polar solvent or non-polar solvent, not as an addition to any other medium.

Example uses of the concentrate/finished product include: liquid form "as-is," diluted, or concentrated; solid form "as-is," diluted, or concentrated; powder form as-is, diluted, or concentrated; incorporation into film(s); incorporation into flake(s); incorporation into sublingual dissolvable pill(s); incorporation into pressed pill(s); incorporation into sublingual dissolvable film(s); incorporation into gum(s), and gummies; incorporation into dried (dehydrated and freeze dried) fruits and flour(s); incorporation into tea(s), coffee(s), and juice(s); production of salt crystal(s) for edible consumption; production of salt crystal(s) for topical use; production of sugar crystal(s) for edible consumption; production of sugar crystal(s) for topical use; and incorporation into gel(s), ointment(s), salve(s), cream(s), and/or lubricant(s) for topical and/or mucosal absorption.

Example percentages of final components ("substances") in a dried/solid form of the concentrate are provided for powder, flake, and salt forms (Examples 1, 2, and 3, respectively) are as follows:

| Substance | Example 1 | Example 2 | Example 3 |
|---|---|---|---|
| Encapsulating material | 47.3% | 43.0% | 26.20% |
| Hydrophobic oil/wax | 49.7% | 45.2% | 26.20% |
| Stabilizer | 0.0% | 8.6% | 3.70% |
| pH altering substance | 3.0% | 2.7% | 1.60% |
| Flavoring components | 0.0% | <0.5% | 0% |
| Salt | 0.0% | 0.0% | 42.40% |

Example percentages of final components in a liquid form of the concentrate (specifically, a gel for topical use) are as follows:

| Substance | Example 1 |
|---|---|
| Cellular material | 2.0% |
| Hydrophobic oil/wax | 1.0% |
| Stabilizer | 20.0% |
| Plant/microbial extracts | 6.0% |
| Fragrances | 0.2% |
| Antioxidants/vitamins | 10.0% |
| Preservative | 1.0% |
| Color | 0.5% |
| Water | 59.3% |

General observations, pertaining to the encapsulation of hydrophobic compounds using cellular material according to embodiments of the present disclosure, are as follows:
- a. Hydrophobic or lipophilic material, in aqueous solution will often separate into a bilayer solution, or seen as droplets (as a liquid) or will often stick to walls of a glass or plastic container (as a solid). With increased concentration of disrupted cellular material in aqueous solution, microencapsulation of hydrophobic material increases (up to a specific maximal point), as seen by reduced bilayer separation of hydrophobic material.
- b. The hydrophobic material and disrupted cellular material are characterized by particular wavelength (nm) absorbance signatures. With increased concentration of disrupted cellular material (up to a specific maximal point), microencapsulation of hydrophobic material increases (up to a specific maximal point), as determined by shifts in absorbance signatures at A280 nm (e.g., general protein absorbance). Although the A280 signature can be used to determine the degree to which the *Spirulina* proteins have been liberated (associated with the degree of cell membrane disruption), other wavelengths are also of interest for characterization purposes and/or for comparing materials before and after encapsulation and/or before and after other steps of the preparation process (e.g., any wavelength between 240 nm and 700 nm).
- c. Increased microencapsulation can be determined by microscopic evidence of structural and aggregation state changes of cellular material before and after implementation of the methods set forth herein.
- d. Disruption of cellular material can be assessed by increased protein absorption at 280 nm, decrease in turbidity as determined by absorption at 600 nm, and/or direct observation of breaking cellular material via microscopy (e.g., brightfield or phase contrast microscopy).
- e. Desirable ranges for cellular disruption range from 40% to 100% lysis, as assessed by methods described in (d), depending on the type of cellular material disrupted.
- f. Fully disrupted cellular material (i.e., about 100% lysis), as assessed by methods described in methods described in (d), risks material decomposition with continued lysis, which then decreases efficiency of encapsulation.
- g. Desirable concentration of cellular materials to increase percentage disruption ranges from about 0.1% to about 10% (w/v). However, desirable encapsulation is often achieved using a greater percent of total cellular material, e.g., ranging from about 0.1% to about 40% (w/v).

Figure 2:
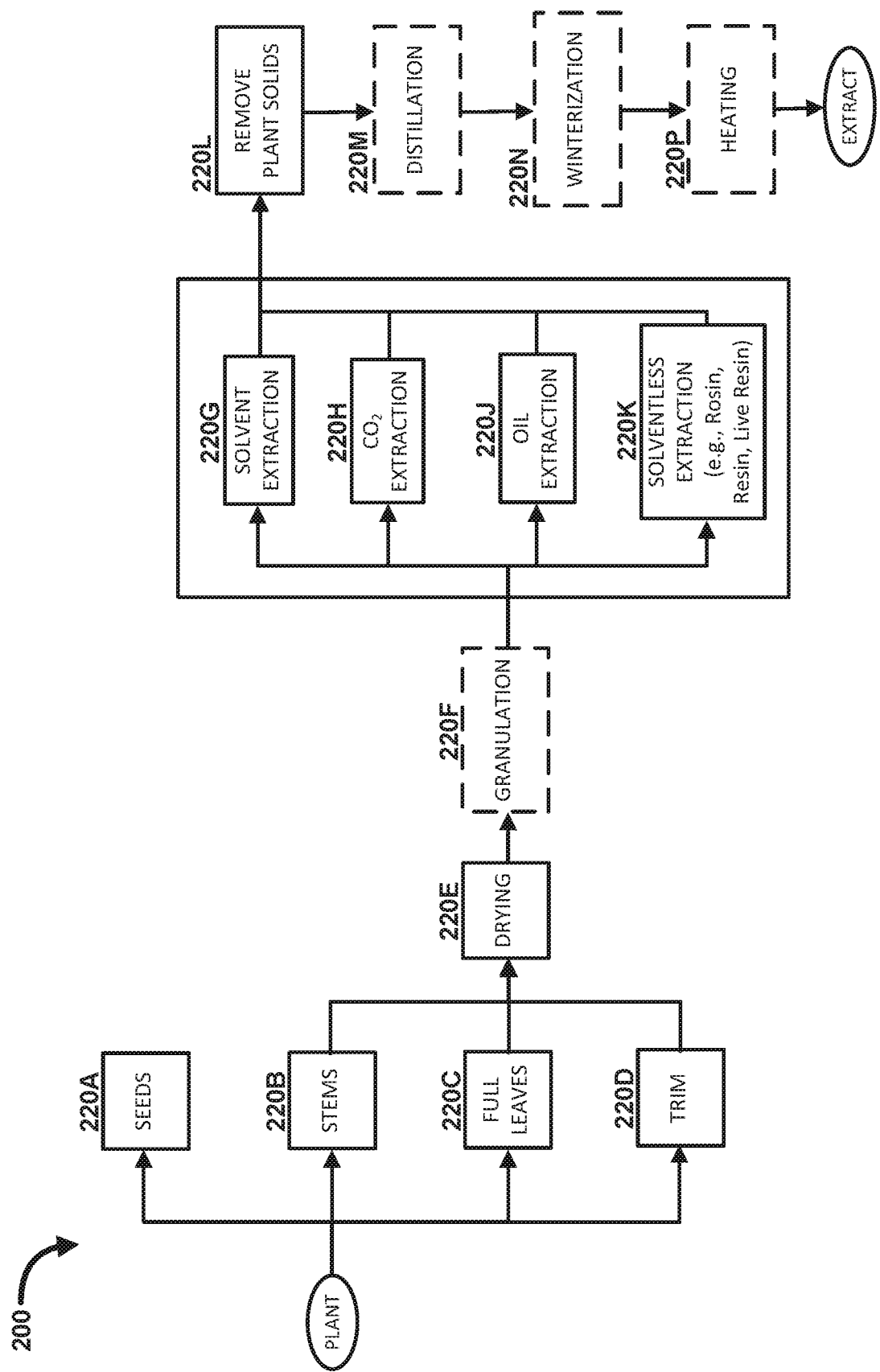
FIG. 2 is a process flow diagram illustrating a method for preparing an extract material, according to some embodiments.

FIG. 2 is a process flow diagram illustrating a method 200 for preparing an extract material, according to some embodiments. As shown in FIG. 2, a plant (e.g., a *Cannabis* plant) can be broken down in multiple parts, including seeds 220A, stems 220B, full leaves 220C, and "trim" (i.e., trimmed portions of leaves) 220D. One or more of the stems 220B, full leaves 220C, and trim 220D can be dried, at 220E, and, optionally, granulated (220F). Next, the dried plant material undergoes an extraction according to one of solvent extraction (220G), $CO_2$ extraction (220H), oil extraction (220J), or solventless extraction (e.g., rosin, resin, or live resin process) (220K). Although shown and described to include only one such extraction process, in some implementations, two or more of solvent extraction (220G), $CO_2$ extraction (220H), oil extraction (220J), a solventless extraction (220K) can be performed on the dried plant material as part of an overall extraction process flow. After extraction (220G, 220H, 220J, or 220K), plant solids are removed (220L), optionally followed by one or more of distillation (e.g., molecular distillation) 220M, winterization 220N, and heating 220P, to obtain a completed extract. "Distillation" can refer to any process of separating one or more components or substances from a liquid mixture by selective boiling and condensation, to produce a "purified" product. In some implementations, the distillation is performed by molecular distillation, to minimize degradation of one or more of the extract component. "Winterization" can refer to any process by which cannabinoids and/or terpenes or other fats are separated from *Cannabis* plant material. Winterization can include an alcohol "wash,"

Figure 3:
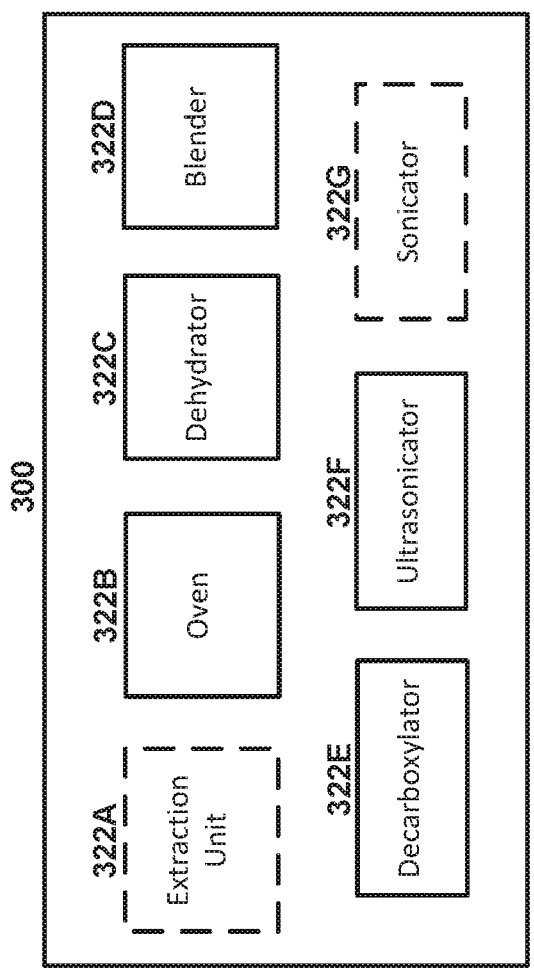
FIG. 3 is a block diagram showing components of a system for encapsulation of an extract material, according to some embodiments.

FIG. 3 is a block diagram showing components of a system 300 for encapsulation of an extract material, according to some embodiments. As shown in FIG. 3, the system 300 can include an oven 322B (e.g., for performing drying as shown at 208 and/or 214 in FIG. 1B), a dehydrator 322C (e.g., for dehydrating as shown at 102P in FIG. 1A), a blender 322D (e.g., for blending of *Spirulina* solution as shown at 102G in FIG. 1A), a decarboxylator 322E (e.g., for performing decarboxylation of extract material as shown at 102B in FIG. 1A), an ultrasonicator 322F (e.g., for ultrasonication as shown at 102H, 102K and/or 102L in FIG. 1A), and, optionally, a sonicator 322G (e.g., for blending of *Spirulina* solution as shown at 102G in FIG. 1A) and/or an extraction unit 322A.

Figure 4A:
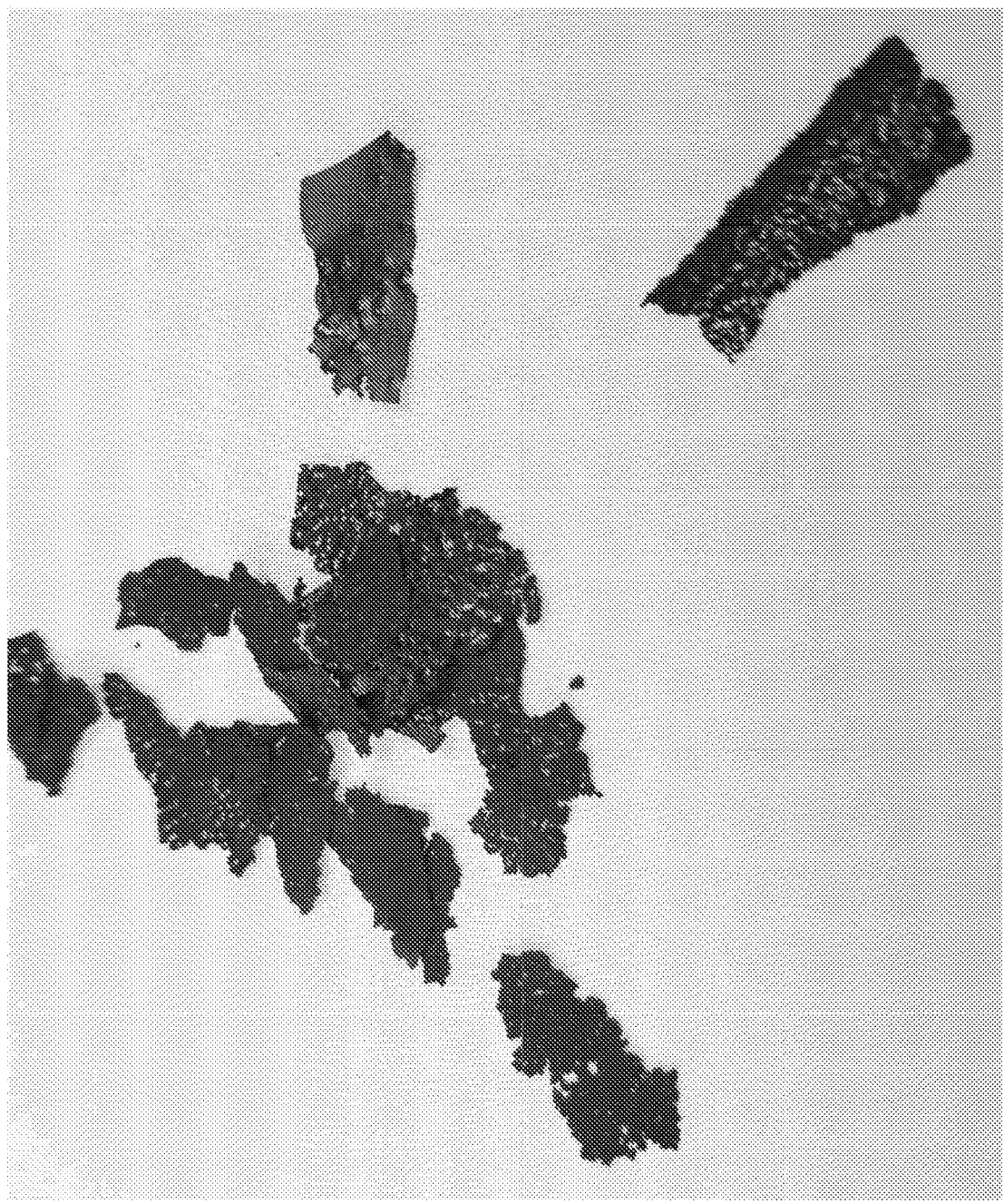
FIGS. 4A-4U are images showing example finished products, according to some embodiments.
Figure 4B:
FIG. 4V is an image showing a comparison of *Spirulina*-based preparations, according to some embodiments.
Figure 4C:
Figure 4D:
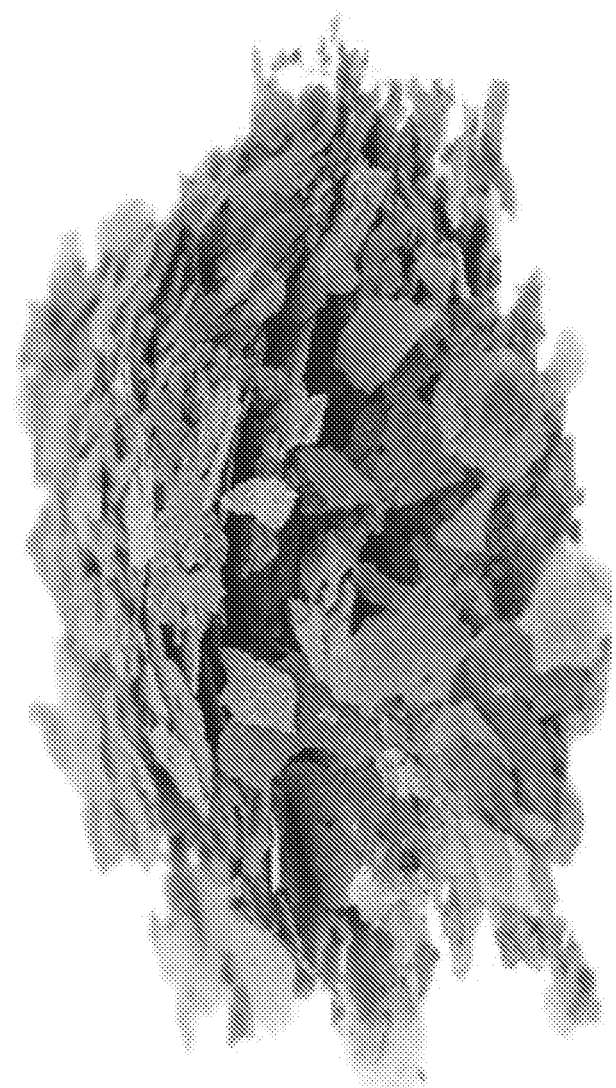
Figure 4F:
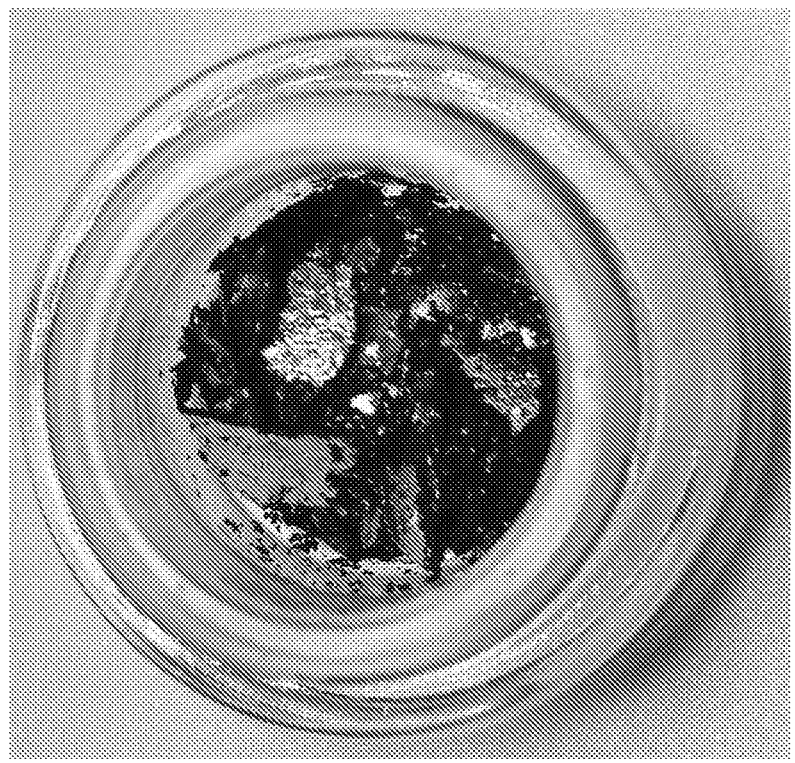

FIGS. 4A-4D are images showing example flake-type finished products, according to some embodiments. The finished product shown in FIG. 4A was prepared using a ratio of 1:1 (w: w) *Spirulina*: Wax (e.g., at step 102I of FIG. 1A), a pour thickness (e.g., at step 102N of FIG. 1A) of about 2.5 mL/in$^2$, a drying duration of about 15 hours. The finished product shown in FIG. 4B was prepared using a ratio of 3:2 (w: w) *Spirulina*: Wax (e.g., at step 102I of FIG. 1A), a pour thickness (e.g., at step 102N of FIG. 1A) of about 2.5 mL/in$^2$, a drying duration of about 15 hours, and the addition of a spearmint oil additive after drying. The finished product shown in FIG. 4C was prepared using a ratio of 1:1 (w: w) *Spirulina*: Wax (e.g., at step 102I of FIG. 1A), a very thin pour thickness (e.g., at step 102N of FIG. 1A) (i.e., a pour thickness significantly less than 2.5 mL/in$^2$), and a drying duration of about 39 hours. As shown in FIG. 4D, the finished product can have a flake-type appearance and texture, and can be highly brittle. Flakes can be irregularly shaped and, unless sorted or otherwise further processed (e.g., broken up, ground, cleaved, filtered, etc.), can vary dramatically in size. Two samples of flake-like finished product, similar to the product shown in FIG. 4D, were age-tested for a period of 22 days, and were found (at the end of the 22-day storage period) to include 22% and 24% cannabinoids, respectively. The results of these age tests are provided herewith, as Appendix D.

Figure 4E:
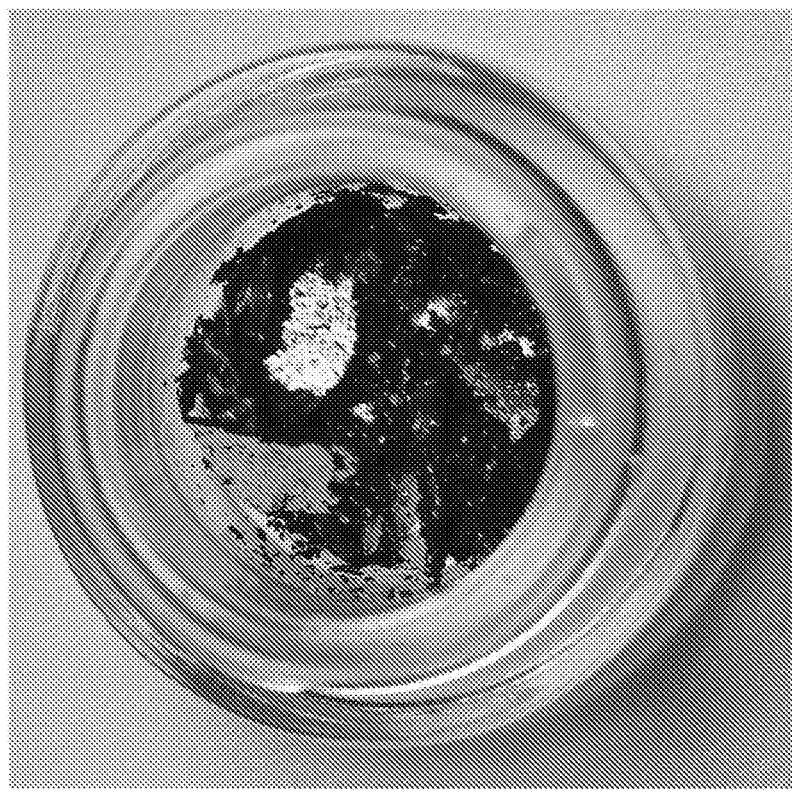
Figure 4H:
Figure 4G:
Figure 4J:
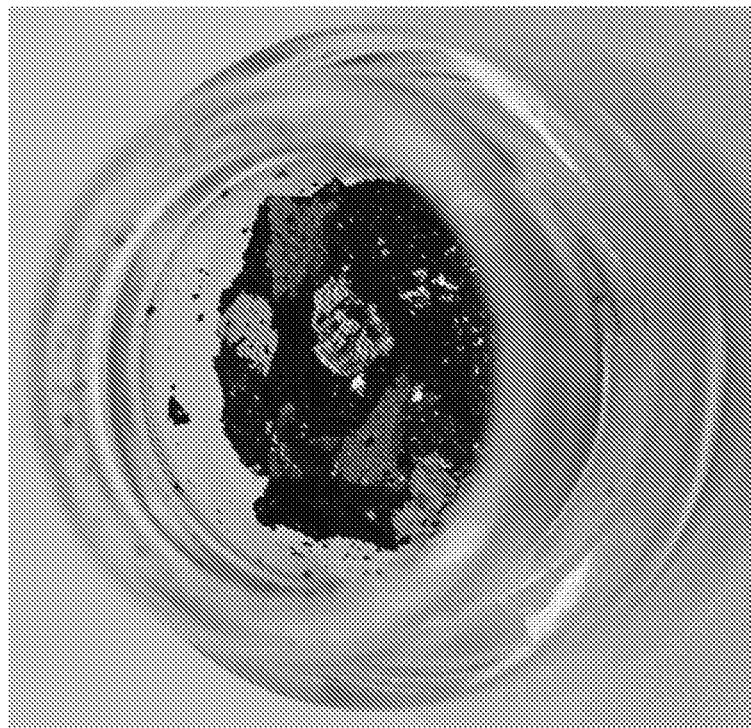
Figure 4I:
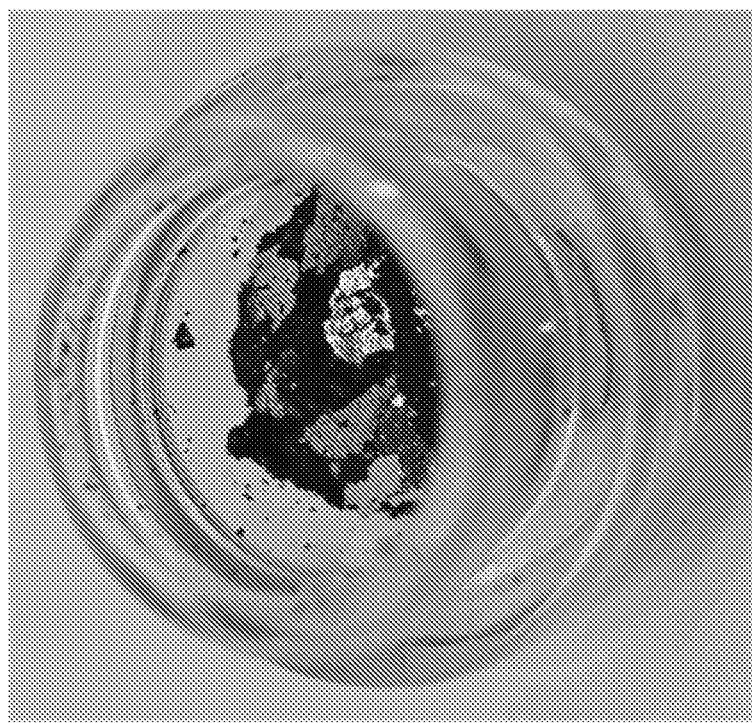
Figure 4L:
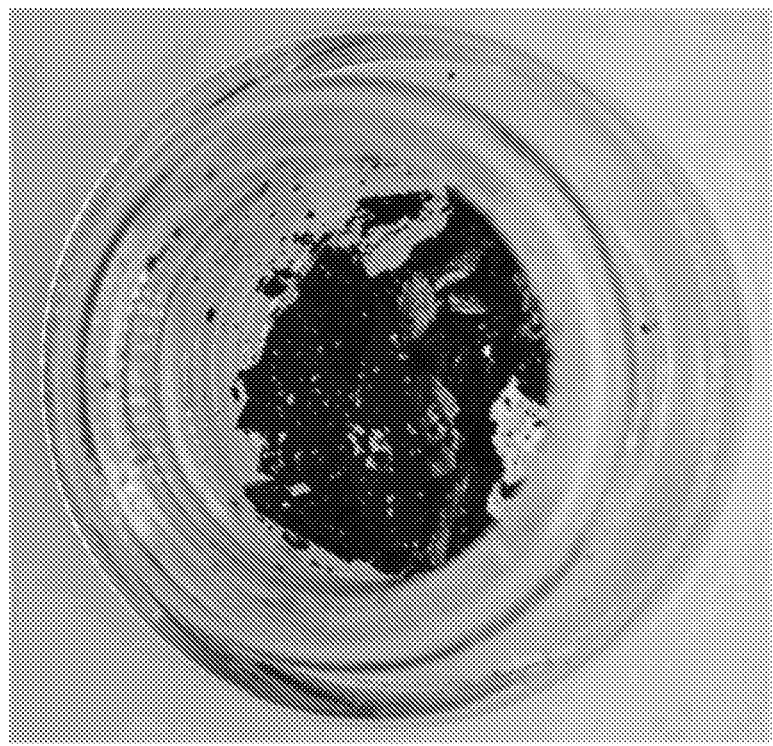
Figure 4K:
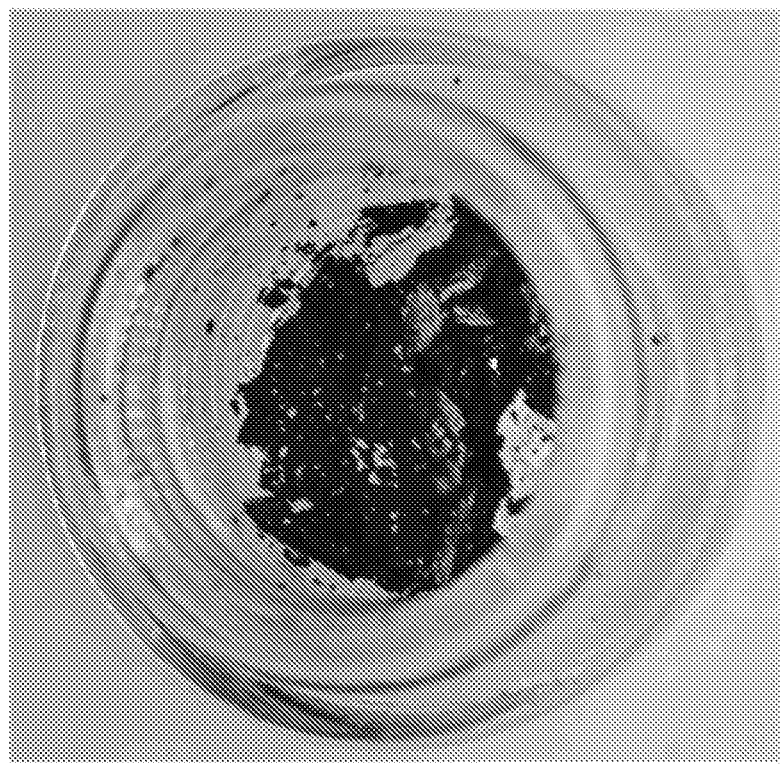
Figure 4N:
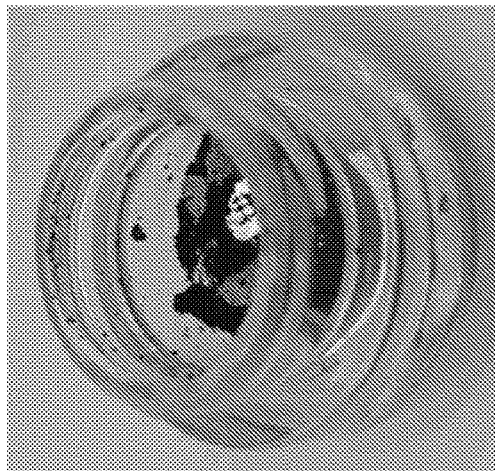
Figure 4O:
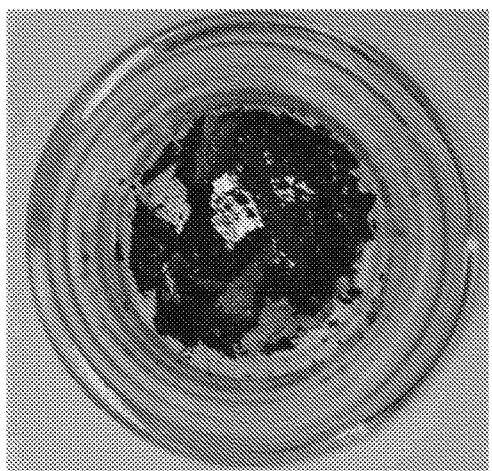
Figure 4M:
Figure 4Q:
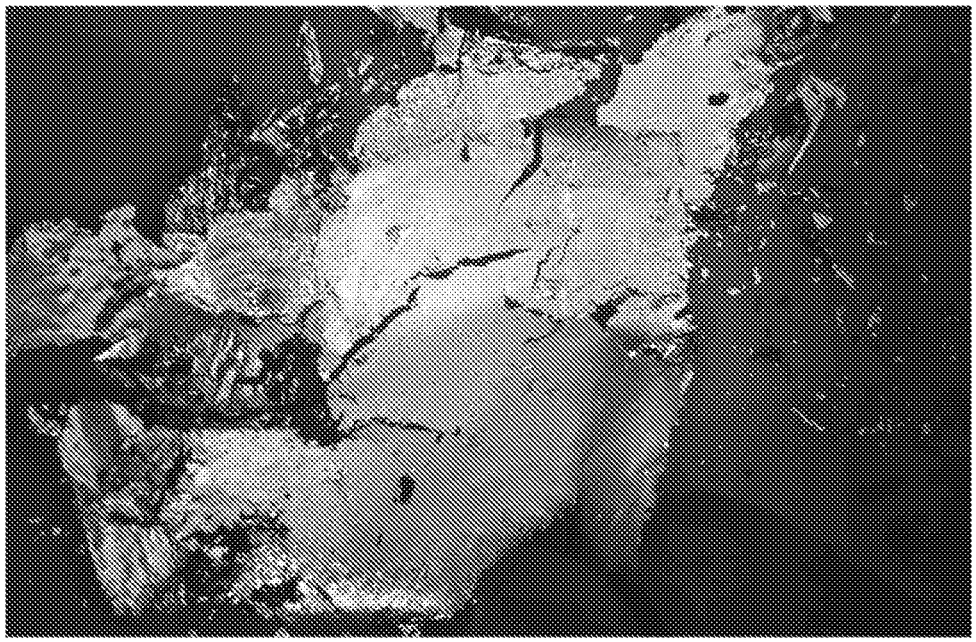
Figure 4P:
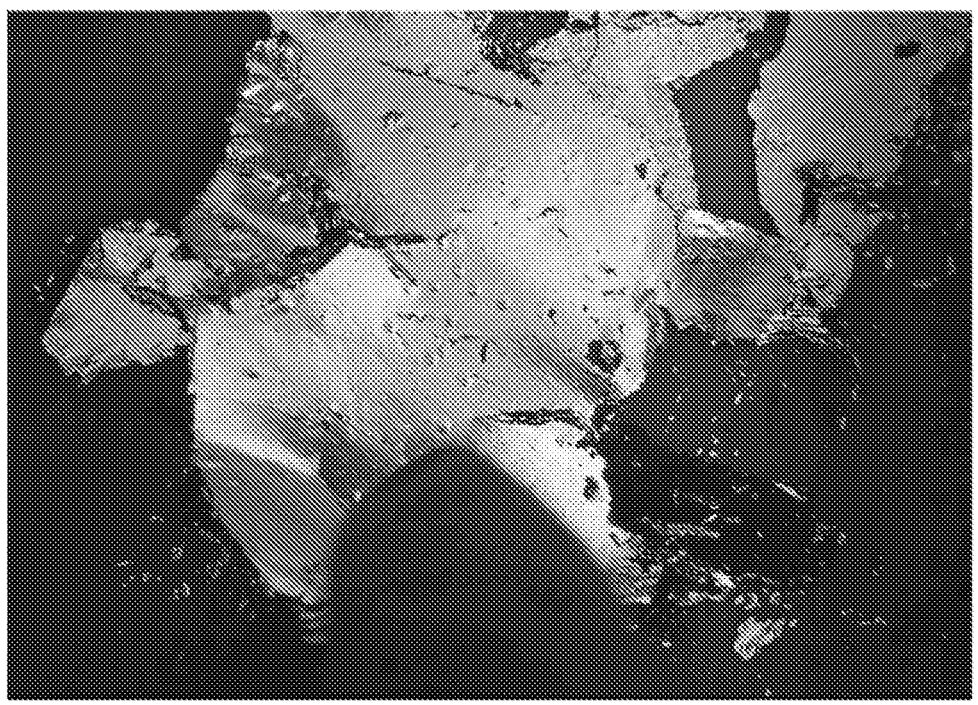
Figure 4S:
Figure 4R:
Figure 4U:
Figure 4T:
Figure 4V:

FIGS. 4E-45 are images showing example flake-type finished products that include gold on at least a surface thereof (e.g., on one major surface, or on both opposing major surfaces of, the finished product), according to some embodiments. FIGS. 4T-4W are images showing example flake-type finished products that include silver on at least a surface thereof (e.g., on one major surface, or on both opposing major surfaces of, the finished product), according to some embodiments. Although shown in FIGS. 4E-4W to include either gold or silver, other comestible/noble metal films could also be applied provided that they are suitable for oral consumption (i.e., are non-toxic), and optionally, chemically inert or substantially chemically inert.

In some embodiments, a method for preparing metallized or metal-containing finished product includes decarboxylation of shatter material at about 115° C. for 40 minutes. *Spirulina* is added directly to the decarboxylated shatter. Separately, water is brought to a boil and then allowed to cool until warm in temperature (e.g., about 32° C. to about 45° C.) before being added to the combined *Spirulina*/decarboxylated shatter. The combined warm water, *Spirulina* and decarboxylated shatter is mixed in a pulsed manner and at a high speed (e.g., using 30-second pulses at about 2,000 rpm), for example in a Silverson batch mixer, to produce a first mixture. The first mixture is sonicated in two stages, first for about 20 minutes at 4° C., and second for about 60 minutes at 60° C. Lecithin, and optionally glycerol, are then added to the sonicated first mixture, in a predetermined amount, suitable amount for the desired finished product (see Table 1, below, and related description), to produce a second mixture. The second mixture is sonicated (e.g., for about 10 minutes at 60° C.), and poured or decanted over an unconstrained (i.e., "free-form," without being confined to a container) to form a layer. The layer is then dehydrated (e.g., at about 165° C. for about 23 hours), resulting in a finished product. Example experimental data for 7 unique batches of double-sided gold flake is summarized in Table 1 below.

crumble. Sample "4" was also prepared according to the procedure set forth above, using about 0.75 grams of *Spirulina*, no glycerol, about 0.3 grams of lecithin, and about 0.75 grams of crumble, such that the final product is about 41.67% crumble. Sample "5" was also prepared according to the procedure set forth above, using about 0.45 grams of *Spirulina*, about 0.325 grams of glycerol, about 0.375 grams of lecithin, and about 0.75 grams of crumble, such that the final product is about 39.47% crumble. Sample "6" was also prepared according to the procedure set forth above, using about 0.525 grams of *Spirulina*, about 0.25 grams of glycerol, about 0.375 grams of lecithin, and about 0.75 grams of crumble, such that the final product is about 39.47% crumble. Sample "7" was also prepared according to the procedure set forth above, using about 0.675 grams of *Spirulina*, about 0.1 grams of glycerol, about 0.375 grams of lecithin, and about 0.75 grams of crumble, such that the final product is about 39.47% crumble.

Prepared samples "1" through "3," in finished product form, had a gummy texture, a flexible film-like structure, and was delicate to handle (i.e., prone to breaking). Prepared sample "4," in finished product form, had a rigid, flake-like structure and texture. Prepared sample "5," in finished product form, exhibited incomplete dissolution, and included relatively large chunks within a solution. Prepared sample "6," in finished product form, was found to have a relatively high mechanical integrity, sheet-like structure that, of the 7 prepared samples, and was most amenable to the application of a metal layer (e.g., via placement of gold leaf, spray application of gold, vapor deposition of gold, etc.) on both sides thereof. Prepared sample "7," in finished product form, was similar to sample "6," but was more flake-like. Sample "7," too, was suitable for the application of a metal layer, but only on one side.

In comparing the prepared samples "1" through "7," it was observed that the amount of lecithin added during the procedure impacts the mouthfeel of the finished product. In other words, glycerol rendered the finished product "smoother" in surface texture, and was observed to function as an emulsifier. It was also observed that the amount of glycerol added during the procedure impacts the mechanical

|  | Number | Spirulina (g) | Glycerol (g) | Lecithin (g) | Crumble (g) | Non-Crumble (g) | % Crumble |
|---|---|---|---|---|---|---|---|
|  | 1 | 0.45 | 0.4 | 0.3 | 0.75 | 1.15 | 39.47% |
|  | 2 | 0.525 | 0.325 | 0.3 | 0.75 | 1.15 | 39.47% |
|  | 3 | 0.675 | 0.175 | 0.3 | 0.75 | 1.15 | 39.47% |
|  | 4 | 0.75 | 0 | 0.3 | 0.75 | 1.05 | 41.67% |
|  | 5 | 0.45 | 0.325 | 0.375 | 0.75 | 1.15 | 39.47% |
| Best consistency | 6 | 0.525 | 0.25 | 0.375 | 0.75 | 1.15 | 39.47% |
|  | 7 | 0.675 | 0.1 | 0.375 | 0.75 | 1.15 | 39.47% |

As shown in Table 1, sample number "1" was prepared (according to the procedure set forth above) using about 0.45 grams of *Spirulina*, about 0.4 grams of glycerol, about 0.3 grams of lecithin, and about 0.75 grams of crumble (e.g., 25 mL of 3% crumble), such that the final product is about 39.47% crumble. Sample "2" was also prepared according to the procedure set forth above, using about 0.525 grams of *Spirulina*, about 0.325 grams of glycerol, about 0.3 grams of lecithin, and about 0.75 grams of crumble, such that the final product is about 39.47% crumble. Sample "3" was also prepared according to the procedure set forth above, using about 0.675 grams of *Spirulina*, about 0.175 grams of glycerol, about 0.3 grams of lecithin, and about 0.75 grams of crumble, such that the final product is about 39.47% flexibility (i.e., resistance to fracture/breaking) of the finished, flake-like product. In other words, glycerol was observed to function as a plasticizer. Adding glycerol, in an amount up to about 15%, served to increase flexibility of the finished product, and render the finished product less flake-like. Glycerol content above about 15% tended to render the finished product more fragile.

In some embodiments, the consistency of the first mixture (including the combined warm water, *Spirulina* and decarboxylated shatter, as discussed above) is dependent upon the pH of the first mixture and/or the second mixture. For example, FIG. 4X is an image showing an example comparison of *Spirulina*-based preparations having pH values of 2, 6 and 8 (from left to right, respectively. As can be observed in FIG. 4X, the solubility, miscibility and/or consistency of the ingredients in the pH 2 mixture was worst (with visible settling at the bottom of the vial), while solubility, miscibility and/or consistency of the ingredients in the pH 8 mixture was best (as can be visually inferred, for example, by the lack of particulate residue on the inner sidewall of the vial).

Figure 5:
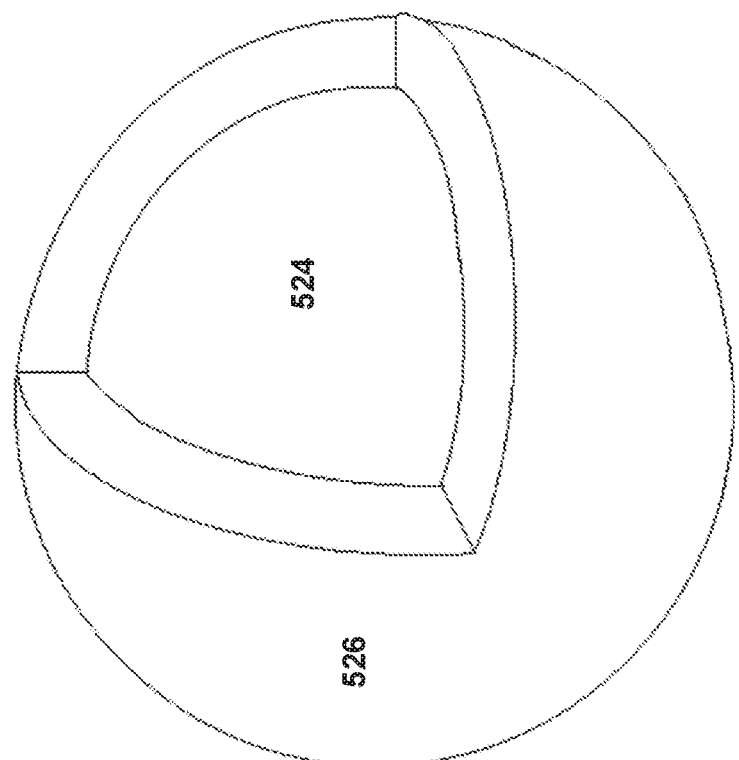
FIG. 5 is an illustration of an example microparticle, according to some embodiments.

FIG. 5 is an illustration of an example microencapsulated extract material (e.g., of a finished product), also referred to herein as a "microparticle" or "microcapsule," according to an embodiment. A microparticle can have a size (e.g., a diameter) of about 1 micrometer (μm) to about 1 millimeter (mm), or about 1 μm to about 5 μm, or about 5 μm to about 10 μm, or about 1 μm to about 10 μm, or about 1 μm to about 100 μm, or about 10 μm to about 100 μm, or about 100 μm to about 500 μm, or about 500 μm to about 1 mm, or about 1 mm to about 5 mm, or about 1 mm to about 2 mm, or about 50 μm to about 75 μm, or about 100 μm to about 250 μm, or about 10 μm to about 500 μm, or about 100 μm to about 5 mm. As shown in FIG. 5, a microparticle can have a core/shell structure (a microcapsule structure) including an extract material core 524 surrounded by an encapsulant 526 (e.g., including *Spirulina*). Although shown to have an overall spherical shape, the microparticle can have any other shape, such as irregular, capsule-shaped, rod-shaped, etc. Depending upon the method of preparation (i.e., according to a method set forth herein), each microparticle in a finished product can have a different composition. Characterization of microparticles can be performed using one or more of scanning electron microscopy (SEM), optical microscope, laser diffraction, fluorescence microscopy, etc.

In some embodiments, the microcapsule and/or finished product containing microcapsules of the disclosure are configured to not include, not include any added, be free from added, be substantially free from added, or be essentially free from added one or more surfactants, one or more artificial surfactants, one or more detergents, one or more emulsifiers, one or more lecithins, one or more lysolethesins, one or more glycolipids, one or more saponins, one or more monoglycerides, one or more sorbitan esters, one or more sucrose esters, one or more saturated fatty acids, one or more unsaturated fatty acids, and/or one or more hydrocolloid polymers. In some embodiments, the microcapsule/microparticle and/or finished product does not include, or is substantially free from, polyethylene glycol ("PEG"). In some embodiments, the microcapsule/microparticle and/or finished product does not include, or is substantially free from, a polysorbate (e.g., polysorbate 20, 40, 60, 65 and/or 80). In some embodiments, the microcapsule/microparticle and/or finished product does not include, or is substantially free from, any Tween compound (e.g., Tween 20, Tween 40, Tween 60, or Tween 80). In some embodiments, the microcapsule/microparticle and/or finished product does not include, or is substantially free from, Polyoxyethene (8) stearate. In some embodiments, the microcapsule/microparticle and/or finished product does not include, or is substantially free from, brominated vegetable oil. In some embodiments, the microcapsule/microparticle and/or finished product does not include, or is substantially free from, succistearin (stearoyl propylene glycol hydrogen succinate). In some embodiments, the microcapsule/microparticle and/or finished product does not include, or is substantially free from, Propanediol 1,2 esters of fatty acids. In some embodiments, the microcapsule/microparticle and/or finished product does not include, or is substantially free from, propylene glycol esters of fatty acids.

In some embodiments, a finished product is in the form of a dissolvable or semi-dissolvable strip or patch for absorption through the gums, cheek, and/or oral mucosal region of a user, for example to reduce pain associated with dental work (e.g., removal of wisdom teeth, dry socket conditions, etc.).

In some embodiments, a finished product is configured for use in one or more of a topical salve, a cream, a gel, a solution, a bath salt, a liquid and/or a solid. In such embodiments, contemplated additives can include (but are not limited to) one or more of the following: *arnica*, calendula, California poppy, olive oil, sunflower oil, avocado oil, beeswax, sage oil, lavender oil, cypress oil, red cedar oil, Chamomile, Lavender oil, Aloe, Mugwort, Himalayan salt, Epsom salt, *eucalyptus*, horsetail, eyebright, shea butter, sweet almond oil, rosehip seed oil, pomegranate seed oil, and cypress essential oil. In some embodiments, the finished product is a liquid, including an aqueous liquid, that includes microencapsulated materials, nanoencapsulated materials, microcapsules, and/or nanocapsules, according to the disclosure. Such embodiments include but are not limited to suspensions, solutions, and/or emulsions. In some embodiments, the microencapsulation/nanoencapsulation provides enhanced stability over time, such as less than a 5%, 10%, 15%, 20% or 25% loss of potency of the active microencapsulated and/or nanoencapsulated active ingredient(s) over time, such as 1 day, 2 days, 3 days, 4 days, 5 days, 6 days, 1 week, 2 weeks, 3 weeks, 4 weeks, 1 month, 2 months, 3 months, or more. In some embodiments, the microencapsulation/nanoencapsulation provides enhanced stability in environment factors, such as exposure to air, light, heat (and/or temperature changes). In some embodiments, the microencapsulation/nanoencapsulation provides enhanced bioavailability. In some embodiments, the finished product (including one or more cannabinoids or *Cannabis* extracts/components) can be used in treatment regimens for and/or treating one or more of chronic pain, paralysis, neuropathy, Crohn's Disease, inflammatory bowel disorders (i.e., IBS and IBD), glaucoma, post-traumatic stress disorder (PTSD), anxiety, seizures, epilepsy, autoimmune disorders, autism, tumors, and/or one or more types of cancer. The finished product can additionally or alternatively be configured for treating nausea and vomiting that are unresponsive to other medications, particular given the improved absorption/bioavailability provided by the disclosed products. In some embodiments, the finished product (including one or more cannabinoids, *Cannabis* extracts/components, including THC and/or CBD) can be used for treatment regimens for dependency on opioids. Accordingly, the disclosure includes methods of alleviating a symptom associated with anxiety, post-traumatic stress disorder, chronic pain, or opiate dependency, paralysis, neuropathy, Crohn's disease, inflammatory bowel disorders, glaucoma, seizures, epilepsy, autism, or cancer comprising administering to a subject one or more formulations/final products according to the disclosure. In some embodiments, a formulation/final product is administered once a day, twice a day, three times a day, four times a day, five times a day, six times a day, or more. In some embodiments, a formulation/final product is administered in the morning, afternoon, evening and at bedtime. In some embodiments, active components of the formulation(s)/final product(s) can be configured for a particular time (e.g., a morning formulation could have relatively more or less active, such as THC, either by quantity or relative proportion to another active, such as CBD, when compared to an evening formulation).

Characterization and Uses of Example Nanoencapsulant/Microencapsulant-Based Solutions As discussed above, methods of the present disclosure can be used for the preparation of a finished product having a liquid form, whether "as-is," diluted, or concentrated. The liquid finished product includes microencapsulated material dissolved within, substantially dissolved within, and/or suspended within a solvent or supernatant. In other words, the final product can be a solution, a suspension, or a mixture.

An example solution-type formulation was prepared, including 3% *Spirulina* and 3% THC wax, by premixing with a Silverson high speed mixer for 30 seconds, followed by 45 minutes of ultrasonication at 10° C. The formulation was then diluted with water, to form a final solution having a ratio of 1:20,000 (formulation: water). The final solution can also be referred to as a THC-infused liquid, or a Spirulinex solution. A volume of 1 mL of the final solution was then analyzed, as described below.

pH Range Testing of Example Solution

Figure 6:
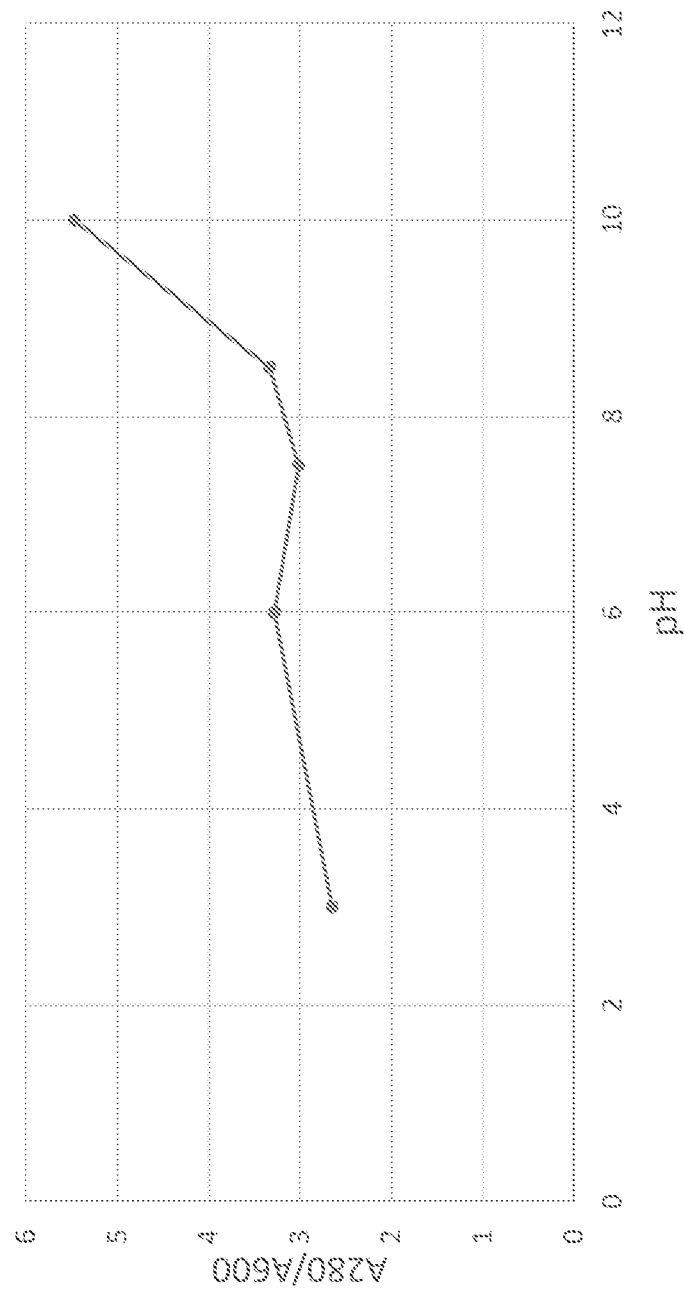
FIG. 6 is a plot of absorbance as a function of pH, for an encapsulant-based solution according to an embodiment.
Figure 7B:
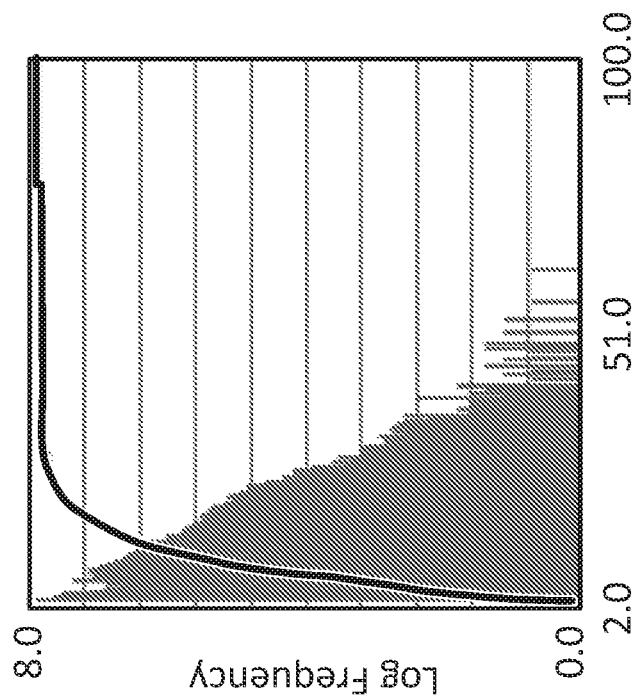
FIGS. 7A-7D are scatterplots showing the distribution of particle sizes within the encapsulant-based solution of FIG. 6.
Figure 7A:
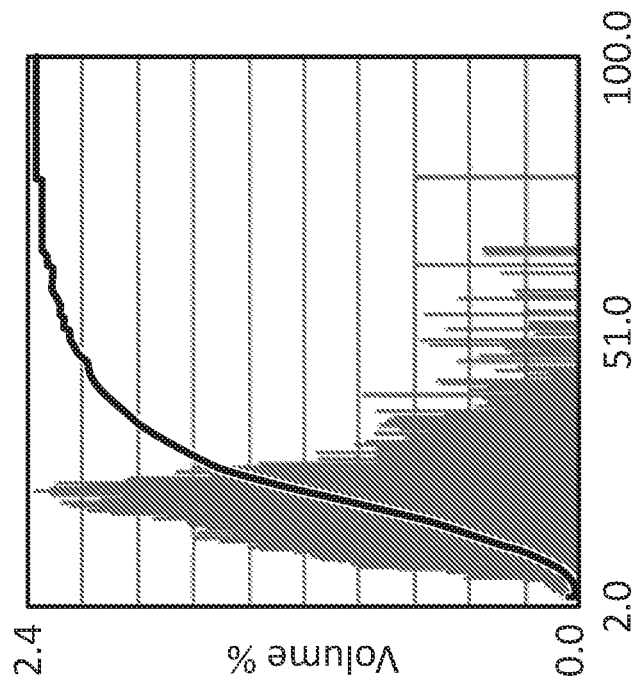
Figures 7C, 7D:
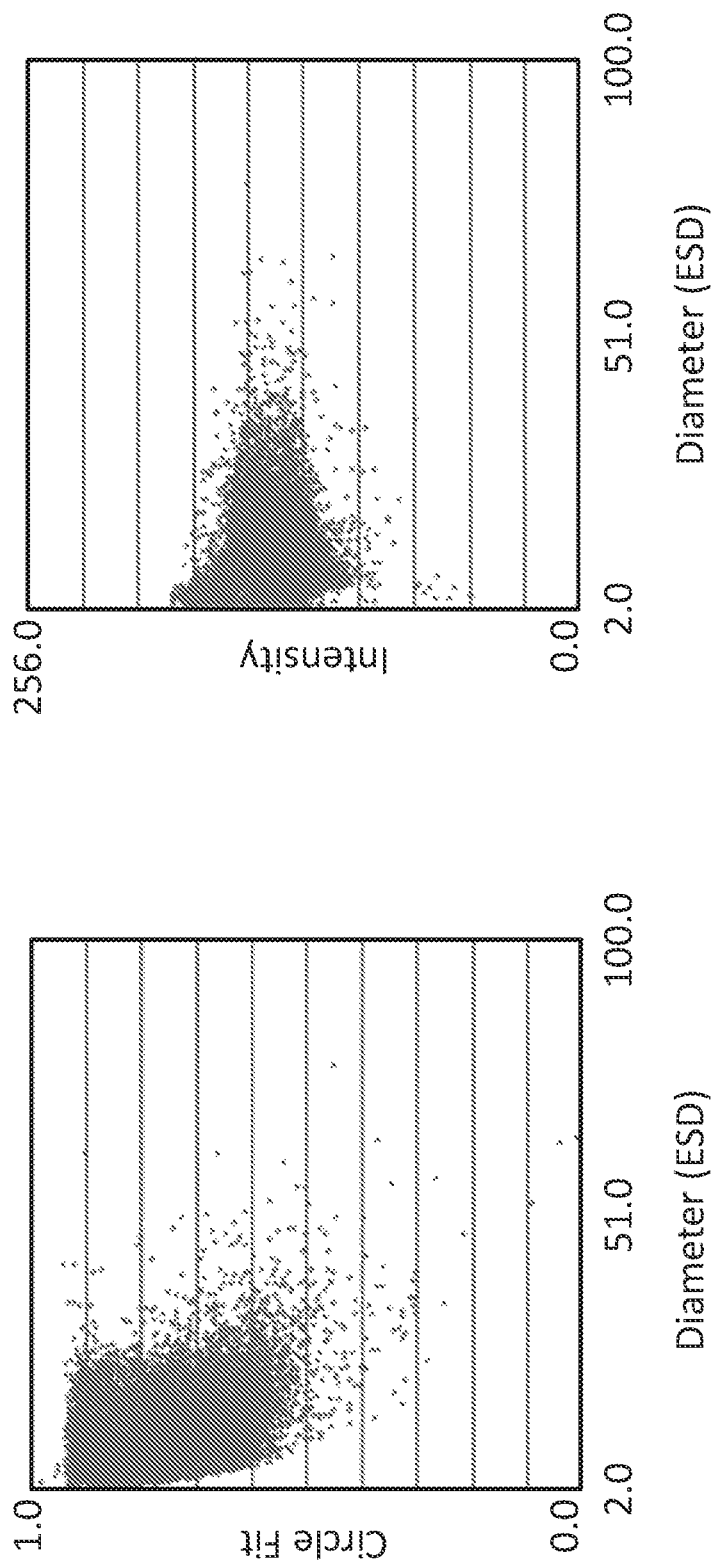

To determine the effect of pH on soluble protein release from cellular material of the final solution, spectrophotometric measurements of absorbance at a wavelength of 280 nm were performed using the final solution. The total cellular material in the solution was assessed using absorbance (or optical density (OD)) measurements, at a wavelength of 600 nm. The ratio of A280/A600 is shown in the plot of FIG. 6, illustrating the protein release from cellular material as a function of pH. As shown in FIG. 6, there is a general increase in protein solubility with increase in pH. As such, the protein is more stable within the solution when exposed to higher pH, while at lower pH, a precipitate forms from the protein "crashing out of" (or precipitating out of)

SOLUTION

Microscale Imaging (>2 um) of Example Solution (Dilution 1:20,000)

Microscopy images of the final solution were obtained using instrumentation developed by Fluid Imaging Technologies, model FlowCam VS1. A 300 uM capillary flow cell was used, with a 4× objective lens and an imaging resolution cutoff of 2 μm. Details pertaining to the instrumentation and experimental settings are provided in Table 1 ("Liquid Imaging Parameters") and Table 5 ("Additional Experimental Details"), below. Particles less than 2 μm were not imaged during microimaging.

Relevant summary statistics, including particle count, mean, minimum maximum, standard deviation, and percent coefficient of variation of parameters such as area, aspect ratio, circle fit, circularity, diameter, edge gradient, and intensity are presented in Table 2 ("Liquid Imaging Summary Statistics"), below. Table 3 ("Particle Size Occurrence") provides the particle counts within each of the listed diameter ranges.

Graphical representations of the particle population based on log frequency, volume %, circle fit, and intensity, each as a function of diameter, are shown in FIGS. 7A-7D (respectively). Furthermore, two distinct populations of particles were identified using edge gradient (a high edge gradient population and a low edge gradient population).

TABLE 1

| Liquid Imaging Parameters | |
| --- | --- |
| Sampling Time | 1 min 33 sec |
| Count | 33323 of 33323 |

TABLE 1-continued

| Liquid Imaging Parameters | |
| --- | --- |
| Particles/ml | 180193669 |
| Droplet mg/L | 454375.3 |
| Solids mg/L | 141938.7 |
| Efficiency | 39.40% |
| PPUI | 51.37 |

TABLE 2

Liquid Imaging Summary Statistics

| Summary Stats | Mean | Min | Max | StdDev | % Coefficient of Variation (% CV) |
| --- | --- | --- | --- | --- | --- |
| Area (ABD) | 31.99 | 1.82 | 1588.76 | 41.87 | 130.87 |
| Aspect Ratio | 0.66 | 0 | 1 | 0.22 | 32.47 |
| Circle Fit | 0.81 | 0 | 1 | 0.1 | 12.9 |
| Circularity | 0.76 | 0.09 | 1 | 0.29 | 38.36 |
| Diameter (Equivalent Spherical Diameter, ESD) | 8.61 | 2.02 | 78.15 | 6.2 | 72.06 |
| Edge Gradient | 46.76 | 2.83 | 158.31 | 25.26 | 54.03 |
| Intensity | 142.7 | 49.55 | 191.6 | 12.22 | 8.56 |

TABLE 3

| Particle Size Occurrence | |
| --- | --- |
| Filter | P/mL |
| 1-2 um ESD | 0 |
| 2-3 um ESD | 29027387 |
| 3-4 um ESD | 18839683 |
| 4-5 um ESD | 10793343 |
| 5-6 um ESD | 15286964 |
| 6-7 um ESD | 14124354 |
| 7-8 um ESD | 15081480 |
| 8-9 um ESD | 12258772 |
| 9-10 um ESD | 9906515 |
| 10-11 um ESD | 8392419 |
| 11-12 um ESD | 6975657 |
| 12-13 um ESD | 6148312 |
| 13-14 um ESD | 4736958 |
| 14-15 um ESD | 3790648 |
| 15-16 um ESD | 3401309 |
| 16-17 um ESD | 3011970 |
| 17-18 um ESD | 2898413 |
| 18-19 um ESD | 2530704 |
| 19-20 um ESD | 2184625 |
| 20-21 um ESD | 1838545 |
| 21-22 um ESD | 1752026 |
| 22-23 um ESD | 1443799 |
| 23-24 um ESD | 1124757 |
| 24-25 um ESD | 848975 |
| 25-26 um ESD | 719196 |
| 26-27 um ESD | 454229 |
| 28-29 um ESD | 324449 |
| 29-30 um ESD | 5407 |

TABLE 3-continued

Particle Size Occurrence

| Filter | P/mL |
|---|---|
| 30-31 um ESD | 216299 |
| 31-32 um ESD | 194670 |
| 32-33 um ESD | 151410 |
| 33-34 um ESD | 167632 |
| 34-35 um ESD | 146002 |
| 35-36 um ESD | 118965 |
| 36-37 um ESD | 59482 |
| 37-38 um ESD | 54075 |
| 38-39 um ESD | 86520 |
| 39-40 um ESD | 43260 |
| 40-41 um ESD | 54075 |
| 41-42 um ESD | 37852 |
| 42-43 um ESD | 16222 |
| 43-44 um ESD | 27037 |
| 44-45 um ESD | 21630 |
| 45-46 um ESD | 16222 |
| 46-47 um ESD | 16222 |
| 47-48 um ESD | 32445 |
| 48-49 um ESD | 32445 |
| 49-50 um ESD | 0 |
| 50-51 um ESD | 16222 |
| 51-52 um ESD | 10815 |
| 52-53 um ESD | 0 |
| 53-54 um ESD | 21630 |
| 54-55 um ESD | 0 |
| 55-56 um ESD | 0 |
| 56-57 um ESD | 16222 |
| 57-58 um ESD | 5407 |
| 58-59 um ESD | 0 |
| 59-60 um ESD | 0 |
| 60-61 um ESD | 5407 |
| 61-62 um ESD | 0 |
| 62-63 um ESD | 10815 |
| 63-64 um ESD | 0 |
| 64-65 um ESD | 10815 |
| 65-66 um ESD | 5407 |
| 66-67 um ESD | 0 |
| 67-68 um ESD | 0 |
| 68-69 um ESD | 0 |
| 69-70 um ESD | 0 |
| 70-71 um ESD | 0 |
| 71-72 um ESD | 0 |
| 72-73 um ESD | 0 |
| 73-74 um ESD | 0 |
| 74-75 um ESD | 0 |
| 76-77 um ESD | 0 |
| 77-78 um ESD | 0 |
| 78-79 um ESD | 5407 |
| 79-80 um ESD | 0 |
| 80-81 um ESD | 0 |
| 81-82 um ESD | 0 |
| 82-83 um ESD | 0 |
| 83-84 um ESD | 0 |
| 84-85 um ESD | 0 |
| 85-86 um ESD | 0 |
| 86-87 um ESD | 0 |
| 87-88 um ESD | 0 |
| 88-89 um ESD | 0 |
| 89-90 um ESD | 0 |
| 90-91 um ESD | 0 |
| 91-92 um ESD | 0 |
| 92-93 um ESD | 0 |
| 93-94 um ESD | 0 |
| 94-95 um ESD | 0 |
| 95-96 um ESD | 0 |
| 96-97 um ESD | 0 |
| 97-98 um ESD | 0 |
| 98-99 um ESD | 0 |
| 99-100 um ESD | 0 |
| 100-1000 um ESD | 0 |

TABLE 4

Particle Size Statistics

| Volume % | Less Than Diameter |
|---|---|
| 10 | 10.64 |
| 25 | 15.49 |
| 50 | 21.53 |
| 75 | 29.97 |
| 90 | 42.41 |

TABLE 5

Additional Experimental Details

| | |
|---|---|
| Particle Segmentation | Dark Threshold 12.00 |
|  | Light Threshold 12.00 |
| Distance to Nearest Neighbor | 10 microns |
| Close Holes | No |
| Basic Size Filter | Diameter (ESD) |
|  | Min 2.00 |
|  | Max 10000.00 microns |
| Advanced Filter | None |
| AutoImage Frame Rate | 7 frames per second |
| Flash Duration | 18.00 microseconds |
| Camera Gain | 0 |

Nanoscale Imaging of Example Solution (Dilution 1:200,000)

Nanoscale measurements of a second final solution, prepared using the formulation described above with reference to the microscale imaging, but further diluted in water (the water having a pH of ~9) to 1:200,000 (instead of 1:20,000 as was done for microimaging), were recorded using a Nanosight instrument designed for Nanoparticle Tracking Analysis, version 2.3. All measurements were performed in triplicate. Sample information for each of three samples is provided in Table 6.

TABLE 6

Nanoimaging Sample Information

| Sample Description | SR...6...1...2018 | SR...6...1...2018 | SR...6...1...2018 |
|---|---|---|---|
| Diluent | water, pH 9 | water, pH 9 | water, pH 9 |
| Pre-treatment | none | none | none |

Figure 8B:
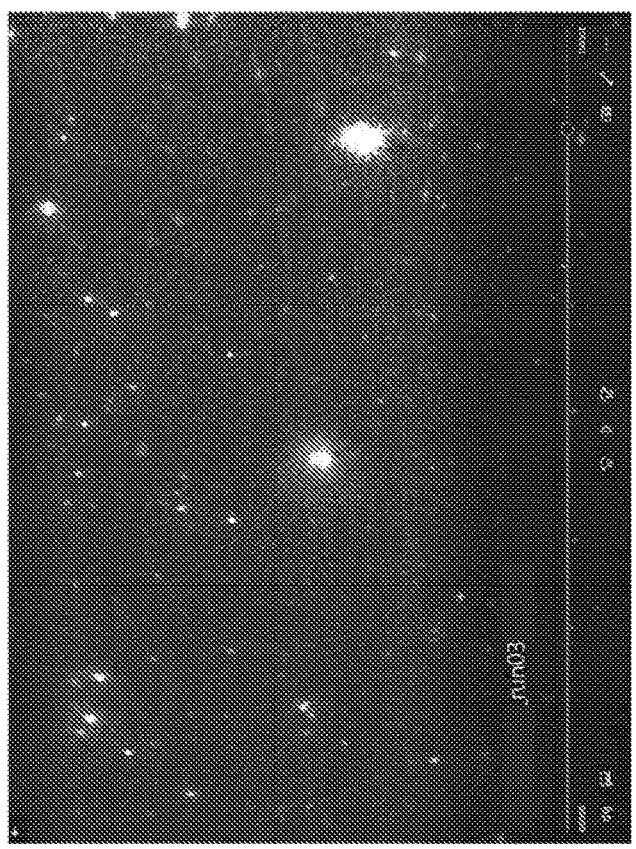
FIGS. 8A-8B are microscopic images of a second encapsulant-based solution according to an embodiment.
Figure 8A:
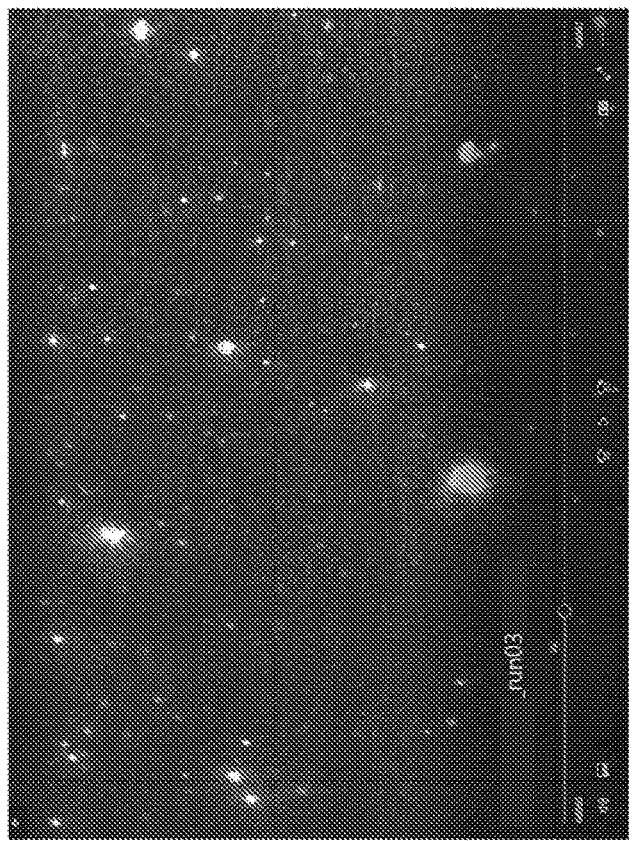

Additional nanoimaging details are provided in Tables 7A-7D, below, and example images of the analyte during processing are shown in FIGS. 8A and 8B.

TABLE 7A

Nanoimaging Details

| | | | |
|---|---|---|---|
| Total Frames | 1860 | 1852 | 1865 |
| Processed Frames | 1860 | 1852 | 1865 |
| Valid Tracks | 11960 | 13479 | 13832 |
| Overall Drift (nm/s) | 6610.65 | 6246.13 | 6600.13 |
| X-Drift (nm/s) | 1801.2 | 1676.69 | 1819.5 |
| Y-Drift (nm/s) | 6360.53 | 6016.88 | 6344.38 |
| Calibration (nm/pixel) | 375 | 375 | 375 |

TABLE 7B

Nanoimaging Instrumentation Settings

| | | | |
|---|---|---|---|
| Background Extract | On | On | On |
| Brightness | 0 | 0 | 0 |
| Gain | 1.00E+00 | 1.00E+00 | 1.00E+00 |
| Blur Size | Auto | Auto | Auto |
| Detection Threshold Type | Multi | Multi | Multi |
| Detection Threshold | 3 | 3 | 3 |
| Min track length | Auto | Auto | Auto |
| Min Expected Size (nm) | Auto | Auto | Auto |
| Max jump distance (nm) | 5.66E+00 | 5.39E+00 | 5.76E+00 |

TABLE 7C

Nanoimaging Measurement Conditions

| | | | |
|---|---|---|---|
| Camera Type | sCMOS | sCMOS | sCMOS |
| Camera Shutter (ms) | 2.40E+01 | 2.40B+01 | 2.40E+01 |
| Camera Gairi | 5.00E+02 | 5.00B+02 | 5.00E+02 |
| Frame rate (fps) | 2.07E+01 | 2.06E+01 | 2.07E+01 |
| Temperature (° C.) | 2.15E+01 | 2.15E+01 | 2.15E+01 |
| Viscosity (cP) | 9.64E-01 | 9.64B-01 | 9.64E-01 |

TABLE 7D

Nanoimaging-Summary of Warnings

| | | | |
|---|---|---|---|
| Low Completed Tracks | No | No | No |
| High Noise | 0 frames | 0 frames | 0 frames |
| High Min Expected Size | Auto | Anto | Auto |
| Drift off | No | No | No |
| Settings Changed Whilst Processing | No | No | No |
| Vibration detected | Vibration detected <10% error | Vibration detected <10% error | Vibration detected <10% error |
| Additional Errors | None | None | None |

Batch results yielded particle (or "droplet") size and finite track length adjustment (FTLA) size distributions ranging from 3 nm to 2,000 nm. Analysis of these distributions are characterized by mean, mode, standard deviations, and "D values" of 10, 50, and 90 (see Table 8, below). A "D value" is defined as the diameter of a particle at which a defined percentage of the sample's mass is comprised of a diameter less than that value. For example, the D50 value is the diameter at which 50% of the particles of the sample have a diameter less than the value. Particle count analysis also reveals total concentration of particles/mL of solution.

TABLE 8

Nanoimaging Size Data-Finite Track Length Adjustment (FTLA) Model Fit

| | | | | Mean | Sid Error |
|---|---|---|---|---|---|
| Mode (nm) | 77 | 79 | 73 | 76.33 | 1.76 |
| Mean (nm) | 189.33 | 197.84 | 183.74 | 190.3 | 4.1 |
| Standard Deviation (nm) | 125.7 | 134.46 | 122.02 | 127.39 | 3.69 |
| D10 (nm) | 74 | 76 | 72 | 74 | 1.15 |
| D50 (nm) | 148 | 150 | 140 | 146 | 3.06 |
| D90 (mm) | 362 | 410 | 370 | 380.67 | 14.85 |
| Chi-squared value | 3.51 | 3.93 | 3.88 | | |

Figures 9A, 9B:
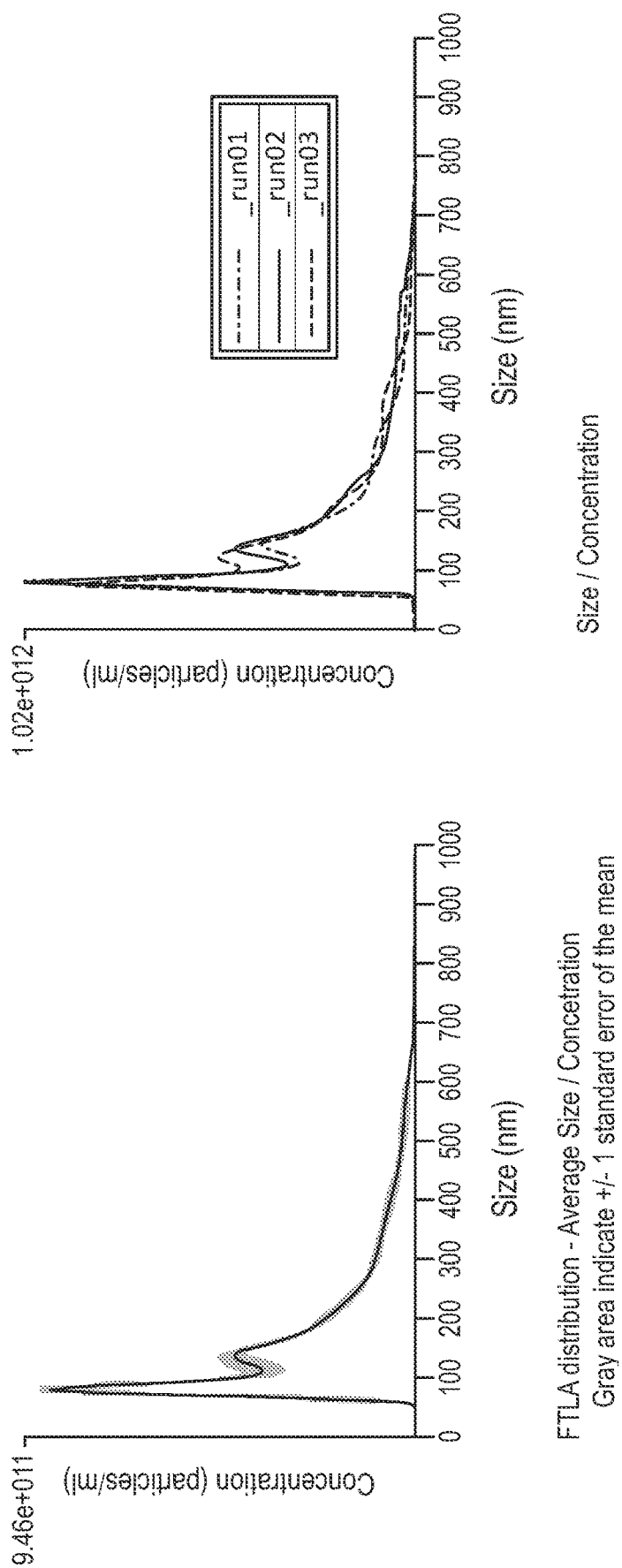
FIGS. 9A-9B are plots showing the distribution of particle sizes within the encapsulant-based solution of FIGS. 8A-8B.

Table 9 shows the concentration-weighted nanoimaging size data for the second final solution. Key features of the analyzed second final solution particle population include: a mean diameter of 174 nm+/−4.1 nm, a mode of 79 nm+/−0.3 nm, and a D50 value of 131 nm+/−3.2 nm. Plots of the particle concentration per particle diameter are presented in FIGS. 9A and 9B, with FIG. 9B showing plots for each of the three sample measurements. The raw data used to generate the plots of FIGS. 9A-9B is presented in Appendix B.

The presence and/or prevalence of nanoscale particle/droplet sizes in final products prepared according to the present disclosure can impact the bioavailability and/or absorption rate of one or more active ingredients (e.g., THC, CBD) when the final product (e.g., solution) is ingested. For example, smaller droplet size may facilitate faster absorption or increased oral bioavailability, such that the related onset of the therapeutic or medicinal effect(s) occurs sooner, whether the final product being consumed is in solution form or in a dry (e.g., flake) form. Further discussion of absorption mechanisms relating to nanoscale materials can be found in: (1) Bapi Gorain, Hira Choudhury, Amit Kundu, Lipi Sarkar, Sanmoy Karmakar, P. Jaisankar, Tapan Kumar Pal, Nanoemulsion strategy for olmesartan medoxomil improves oral absorption and extended antihypertensive activity in hypertensive rats, Colloids and Surfaces B: Biointerfaces, Volume 115, 2014, Pages 286-294, ISSN 0927-7765; and (2) Rabea Parveen, Sanjula Baboota, Javed Ali, Alka Ahuja, Suruchi S. Vasudev, Sayeed Ahmad, Oilk absed nanocarrier for improved oral delivery of silymarin: In vitro and in vivo studies, International Journal of Pharmaceutics, Volume 413, Issues 1-2, 2011, Pages 245-253, ISSN 0378-5173, each of which is incorporated by reference herein in its entirety for all purposes.

TABLE 9

Nanoimaging Size Data-Concentration Weighted

| | | | | Mean | Std Error |
|---|---|---|---|---|---|
| Mode (nm) | 79 | 79 | 78 | 78.67 | 0.33 |
| Mean (nm) | 172.99 | 181 | 166.94 | 173.64 | 4.07 |
| Standard Deviation (nm) | 139.59 | 148.48 | 138 | 142.02 | 3.26 |
| D10 (nm) | 65 | 68 | 64 | 65.67 | 1.2 |
| D50 (nm) | 131 | 136 | 125 | 130.67 | 3.18 |
| D90 (nm) | 324 | 341 | 314 | 326.33 | 7.88 |
| Average # centres/frame | 159.43 | 173.71 | 178.64 | 170.6 | 5.76 |
| Dilution factor (concentrations below are adjusted for this factor) | 200000 | 200000 | 200000 | | |

TABLE 9-continued

Nanoimaging Size Data-Concentration Weighted

|  |  |  |  | Mean | Std Error |
|---|---|---|---|---|---|
| Average # particles/frame | 143.95 | 157.27 | 163.6 | 154.94 | 5.79 |
| Equivalent particle concentration (particles/ml) | 8.15E+13 | 8.90E+13 | 9.26E+13 | 8.77E+13 | 3.28E+12 |
| Selected average # particles/frame | 0 | 0 | 0 | 0 | 0 |
| Selected equivalent particle concentration (particles/ml) | 0.00E+00 | 0.00E+00 | 0.00E+00 | 0.00E+00 | 0.00E+00 |

The overall results from the nanoimaging of the 1:200,000 diluted second final solution are presented in Table 13, below. FTLA Model Fit Data is presented in Appendix C.

TABLE 13

Nanoimaging-Overall Results

BATCH AVERAGE RESULTS:

| Sample: | | FTLA Size Distribution: | Mean: 190.3 +/− 4.1 nm |
|---|---|---|---|
| Included files: | _num01 | | Mode: 76 +/− 1.8 nm |
| | _num02 | | SD: 127.4 +/− 3.7 nm |
| | _num03 | | D10: 74 +/− 1.2 nm |
| | | | D50: 146.0 +/− 3.1 nm |
| Dispersant/Diluent: | water, pH 9 | | D90: 381 +/− 14.8 nm |
| Pretreatment | none | Size Distribution: | Mean: 174 +/− 4.1 nm |
| | | | Mode: 79 +/− 0.3 nm |
| | | | SD: 142 +/− 3.3 nm |
| | | | D10: 66 +/− 1.2 nm |
| | | | D50: 131 +/− 3.2 nm |
| | | | D90: 326 +/− 7.9 nm |
| | | Dilution factor: | 200000 |
| | | Total Concentration: | 154.94 +/− 5.79 particles/frame |
| | | | 8.77e+013 +/− 3.28e+012 particles/ml |
| | | Total Completed Tracks: | 39271 |
| | | Average Drift Velocity: | 6488 nm/s |
| CAPTURE SETTINGS | | | |
| | | Camera Type: | aCMOS |
| | | Shutter length: | Varied |
| | | Shutter setting: | 1200 |
| | | Camera gain: | 500 |
| | | Frame rate: | Varied |
| ANALYSIS SETTINGS | | | |
| | | Background Extract: | On |
| | | Detection Threshold: | 3-Multi |
| | | Blur: | AUTO |
| | | Min track length: | AUTO |
| | | Min expected size: | AUTO |
| | | Temperature: | 21.5, 21.5, 21.5° C. |
| | | Viscosity: | 0.96, 0.96, 0.96 cP |

Without wishing to be bound by theory, it is believed that the encapsulation occurring during the preparation of the formulations described herein is accomplishes, at least in part, by virtue of one or more key proteins (e.g., apcE Phycobilisome core-membrane linker polypeptide (Anchor polypeptide LCM), cpcA C-phycocyanin alpha subunit, apcB Allophycocyanin beta subunit, cpcB C-phycocyanin beta subunit, ribH 6,7-dimethyl-8-ribityllumazine synthase protease, ATP-dependent zinc-metallo (fragment), etc.) of Arthrospira platensis or edible versions of the genus Arthrospira, which are liberated during the preparation process. Previous proteomic studies of Arthrospira platensis have identified on the order of 1,000 proteins. Appendix A includes a listing of such proteins, with data such as isoelectric point (pI) and molecular weight (MW). Additional details relating to proteomic studies of Arthrospira platensis can be found in Matallana-Surget S, Derock J, Leroy B, Badri H, Deschoenmaeker F, Wattiez R (2014) Proteome-Wide Analysis and Diel Proteomic Profiling of the Cyanobacterium Arthrospira platensis PCC 8005. PLOS ONE 9(6): e99076, each of which is incorporated by reference herein in its entirety for all purposes.

All combinations of the foregoing concepts and additional concepts discussed herewithin (provided such concepts are not mutually inconsistent) are contemplated as being part of the subject matter disclosed herein. The terminology explicitly employed herein that also may appear in any disclosure incorporated by reference should be accorded a meaning most consistent with the particular concepts disclosed herein.

The skilled artisan will understand that the drawings primarily are for illustrative purposes, and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

To address various issues and advance the art, the entirety of this application (including the Cover Page, Title, Headings, Background, Summary, Brief Description of the Drawings, Detailed Description, Embodiments, Abstract, Figures, Appendices, and otherwise) shows, by way of illustration, various embodiments in which the embodiments may be practiced. The advantages and features of the application are of a representative sample of embodiments only, and are not exhaustive and/or exclusive. Rather, they are presented to assist in understanding and teach the embodiments, and are not representative of all embodiments. As such, certain aspects of the disclosure have not been discussed herein. That alternate embodiments may not have been presented for a specific portion of the innovations or that further undescribed alternate embodiments may be available for a portion is not to be considered to exclude such alternate embodiments from the scope of the disclosure. It will be appreciated that many of those undescribed embodiments incorporate the same principles of the innovations and others are equivalent. Thus, it is to be understood that other embodiments may be utilized and functional, logical, operational, organizational, structural and/or topological modifications may be made without departing from the scope and/or spirit of the disclosure. As such, all examples and/or embodiments are deemed to be non-limiting throughout this disclosure.

Also, no inference should be drawn regarding those embodiments discussed herein relative to those not discussed herein other than it is as such for purposes of reducing space and repetition. For instance, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure.

The term "automatically" is used herein to modify actions that occur without direct input or prompting by an external source such as a user. Automatically occurring actions can occur periodically, sporadically, in response to a detected event (e.g., a user logging in), or according to a predetermined schedule.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Various concepts may be embodied as one or more methods, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Put differently, it is to be understood that such features may not necessarily be limited to a particular order of execution, but rather, any number of threads, processes, services, servers, and/or the like that may execute serially, asynchronously, concurrently, in parallel, simultaneously, synchronously, and/or the like in a manner consistent with the disclosure. As such, some of these features may be mutually contradictory, in that they cannot be simultaneously present in a single embodiment. Similarly, some features are applicable to one aspect of the innovations, and inapplicable to others.

In addition, the disclosure may include other innovations not presently described. Applicant reserves all rights in such innovations, including the right to embodiment such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the embodiments or limitations on equivalents to the embodiments. Depending on the particular desires and/or characteristics of an individual and/or enterprise user, database configuration and/or relational model, data type, data transmission and/or network framework, syntax structure, and/or the like, various embodiments of the technology disclosed herein may be implemented in a manner that enables a great deal of flexibility and customization as described herein.

All definitions, as defined and used herein, should be understood to control over dictionary definitions, definitions in documents incorporated by reference, and/or ordinary meanings of the defined terms.

As used herein, in particular embodiments, the terms "about" or "approximately," when preceding a numerical value, indicate the specified value plus or minus a range of 10%. For example, a duration of "about 30 minutes" refers to a duration of from 27 minutes to 33 minutes. Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. That the upper and lower limits of these smaller ranges can independently be included in the smaller ranges is also encompassed within the disclosure, subject to any specifically excluded limit in the stated range. Where the stated range includes one or both of the limits, ranges excluding either or both of those included limits are also included in the disclosure.

The indefinite articles "a" and "an," as used herein in the specification and in the embodiments, unless clearly indicated to the contrary, should be understood to mean "at least one."

The phrase "and/or," as used herein in the specification and in the embodiments, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the embodiments, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the embodiments, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the embodiments, shall have its ordinary meaning as used in the field of patent law.

As used herein in the specification and in the embodiments, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the embodiments, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While specific embodiments of the present disclosure have been outlined above, many alternatives, modifications, and variations will be apparent to those skilled in the art. Accordingly, the embodiments set forth herein are intended to be illustrative, not limiting. Various changes may be made without departing from the spirit and scope of the disclosure.

What is claimed is:

1. A method for preparing an encapsulated *cannabis* comprising:
   a) providing a *cannabis* extract which includes a shatter of *cannabis*, a wax of *cannabis*, a crumble of *cannabis*, or a *cannabis* butter;
   b) providing distilled water;
   c) raising the pH of the distilled water to greater than 7, to produce a raised-pH water;
   d) preparing an aqueous solution including the raised-pH water and *Spirulina*, wherein the aqueous solution has between 1% to 10% weight volume of *Spirulina*;
   e) using ultrasonication to disrupt the aqueous solution;
   f) combining the *cannabis* extract and the disrupted aqueous solution to form a *cannabis* disrupted aqueous solution; and
   g) drying the *cannabis* disrupted aqueous solution to form the encapsulated *cannabis*.

2. The method of claim 1, wherein the *cannabis* extract has THC.

3. The method of claim 1, wherein the preparing of the aqueous solution includes mixing to at least partially liberate proteins of the *Spirulina*.

4. The method of claim 1, further comprising:
   diluting the aqueous solution to a predetermined dilution level between 1:1,000 to 1:200,000.

5. The method of claim 1, further comprising:
   decarboxylating the *cannabis* extract before combining the *cannabis* extract and the disrupted aqueous solution.

6. The method of claim 1, further comprising:
   dispensing the first mixture onto a substrate to form a layer on the substrate before drying the *cannabis* disrupted aqueous solution to form the encapsulated *cannabis*.

7. The method of claim 1, further comprising:
   forming a first mixture that includes the encapsulated *cannabis*; and
   dispensing the first mixture onto a substrate to form a layer on the substrate before drying the *cannabis* disrupted aqueous solution to form the encapsulated *cannabis*.

8. The method of claim 1, further comprising:
   using ultrasonication to at least partially liberate proteins of the *Spirulina*.

9. The method of claim 1, further comprising:
   combining the encapsulated *cannabis* with a solvent to form a liquid finished product that is a solution or a suspension.

10. The method of claim 1, further comprising:
    adding acid to the first mixture to lower the pH level of the intermediate mixture to between 3 and 5 before using ultrasonication to disrupt the aqueous solution.

11. A method for preparing an encapsulated *cannabis* comprising:
    a) providing a *cannabis* extract;
    b) providing distilled water;

c) raising the pH of the distilled water to greater than 7, to produce a raised-pH water;
d) preparing an aqueous solution including the raised-pH water and *Spirulina*, wherein the aqueous solution has *Spirulina*;
e) using ultrasonication to disrupt the aqueous solution;
f) combining the *cannabis* extract and the disrupted aqueous solution to form a *cannabis* disrupted aqueous solution; and
g) drying the *cannabis* disrupted aqueous solution to form the encapsulated *cannabis*.

12. The method of claim 11, wherein the *cannabis* extract has THC.

13. The method of claim 1, wherein the preparing of the aqueous solution includes mixing to at least partially liberate proteins of the *Spirulina*.

14. The method of claim 11, further comprising:
diluting the aqueous solution to a predetermined dilution level between 1:1,000 to 1:200,000.

15. The method of claim 11, further comprising:
decarboxylating the *cannabis* extract before combining the *cannabis* extract and the disrupted aqueous solution.

16. The method of claim 11, further comprising:
dispensing the first mixture onto a substrate to form a layer on the substrate before drying the *cannabis* disrupted aqueous solution to form the encapsulated *cannabis*.

17. The method of claim 11, further comprising:
forming a first mixture that includes the encapsulated *cannabis*; and
dispensing the first mixture onto a substrate to form a layer on the substrate before drying the *cannabis* disrupted aqueous solution to form the encapsulated *cannabis*.

18. The method of claim 11, further comprising:
using ultrasonication to at least partially liberate proteins of the *Spirulina*.

19. The method of claim 11, further comprising:
combining the encapsulated *cannabis* with a solvent to form a liquid finished product that is a solution or a suspension.

20. The method of claim 11, further comprising:
adding acid to the first mixture to lower the pH level of the intermediate mixture to between 3 and 5 before using ultrasonication to disrupt the aqueous solution.

* * * * *